(12) United States Patent
Liao et al.

(10) Patent No.: US 7,647,188 B2
(45) Date of Patent: Jan. 12, 2010

(54) SYSTEMS AND METHODS FOR PROCESSING NUCLEIC ACID CHROMATOGRAMS

(75) Inventors: Guochun Liao, Belmont, CA (US); Jonathan A. Usuka, Palo Alto, CA (US); Gary Allen Peltz, Redwood City, CA (US)

(73) Assignee: F. Hoffmann-La Roche AG, Basel (CH)

( * ) Notice: Subject to any disclaimer, the term of this patent is extended or adjusted under 35 U.S.C. 154(b) by 650 days.

(21) Appl. No.: 10/942,538

(22) Filed: Sep. 15, 2004

(65) Prior Publication Data

US 2006/0058969 A1 Mar. 16, 2006

(51) Int. Cl.
G06F 19/00 (2006.01)
(52) U.S. Cl. .......................................... 702/20; 702/19
(58) Field of Classification Search ........................ None
See application file for complete search history.

(56) References Cited

U.S. PATENT DOCUMENTS

| 6,195,449 B1 | 2/2001 | Bogden et al. |
| 6,596,140 B2 | 7/2003 | Nordman et al. |
| 2004/0009521 A1 | 1/2004 | Liu et al. |

FOREIGN PATENT DOCUMENTS

| EP | 05 02 0018 | 6/2006 |
| SG | 200505937-3 | 3/2006 |
| WO | WO 98/00708 | 1/1998 |
| WO | WO 03 029487 A2 | 4/2003 |
| WO | WO 03/029487 A3 | 4/2003 |

OTHER PUBLICATIONS

Thomann et al. "The Use of Sequence Analysis for Homozygote and Heterozygote Base Variation Discovery" in Molecular Genetic Epidemiology: A Laboratory Perspective (2002) Springer Verlag, Chapter 8, Ian N.M. Day (Ed.).*
Tibbets. "Raw Data File Formats, and the Digital and Analog Raw Data Streams of the ABI Prism™ 377 DNA Sequencer," Aug. 1995, pp. 1-35.
Amersham Biosciences, "MegaBACE 1000 Instrument Administrator's Guide, v 2.0," product user manual, Oct. 1999. pp. i-xvii, pp. 1-1 to Index-5.
Ewing et al., "Base-Calling of Automated Sequencer Tracers Using Phred.: I. Accuracy Assessment," Genome Research, 1998, vol. 8, pp. 175-185.
Ewing et al., "Base-Calling of Automated Sequencer Tracers Using Phred.: II. Error Probabilities," Genome Research, 1998, vol. 8, pp. 186-194.
Gene Codes Corp., "Sequencher Tour Guide," product brochure, 2000, pp. 1-14.
Laitinen et al., "Association Study of the Chromosomal Region Containing the FCER2 Gene Suggests It Has a Regulatory Role in Atopic Disorders," Am J Respir Crit Care Med, 2000, vol. 161, pp. 700-706.
Zhang et al., "HapScope: a software system for automated and visual analysis of functionally annotated haplotypes," Nucleic Acids Research, 2002, vol. 30, No. 23, pp. 5213-5221.
Cheng et al., "A Multilocus Genotyping Assay for Candidate Markers of Cardiovascular Disease Risk," Genome Research, 1999, vol. 9, pp. 936-949.
Lipshutz et al., 1994, "DNA Sequence Confidence Estimation," Genomics 19: 417-424.
Giddings et al., 1998, "A Software System for Data Analysis in Automated DNA Sequencing," Genome Research: 644-665.
Nickerson et al., 1997, "PolyPhred: automating the detection and genotyping of single nucleotide substitutions using fluorescence-based resequencing," Nucleic Acids Research 25: 2745-2751.
Phelps et al., 1995, "Efficient, Automatic Detection of Heterozygous Bases During Large-Scale DNA Sequence Screening," BioTechniques 19: 984-989.
Hattori et al., 1992, "Orphan Peak Analysis: A Novel Metod for Detection of Point Mutations Using an Automated Fluorescence DNA Sequencer," Genomics 15: 415-417.
Kwok et al., 1994, "Comparative Analysis of Human DNA Variations by Fluorescence-Based Sequencing of PCR Products," Genomics 23: 138-144.
McGinnis et al., 1995, "Automated, solid-phase sequencing of DRB region genes using T7 sequencing chemistry and dye-labeled primers," Tissue Antigens 46: 173-179.
Rozemuller et al., 1993, "Assignment of HLA-DPB Alleles by Computerized Matching Based Upon Sequemce Data," Human Immunology 37: 207-212.
Versluis et al., 1993, "High-Resolution HLA-DPB Typing Based Upon Computerized Analysis of Data Obtained by Fluorescent Sequencing of the Amplified Polymorphic Exon 2," Human Immunology 38: 277-283.

* cited by examiner

Primary Examiner—Lori A Clow
(74) Attorney, Agent, or Firm—Brett Lovejoy; Jones Day

(57) ABSTRACT

Computer systems, computer program products and methods for processing an input nucleic acid chromatogram having a plurality of substantially simultaneous traces. Each trace in the plurality of traces has a plurality of datapoints. Each respective datapoint in each of the plurality of datapoints represents a signal amplitude at a position in the trace corresponding to the respective datapoint. A first peak is identified in a first trace that is substantially overlapping a second peak in a second trace in the plurality of traces. The first peak is outputted to a first output homozygous representation and the second peak is outputted to a second output homozygous representation. The first output homozygous representation is a first homozygous sequence representation or a first homozygous nucleic acid chromatogram corresponding to the input nucleic acid chromatogram. The second output homozygous representation is a second homozygous sequence representation or second homozygous nucleic acid chromatogram of the input nucleic acid chromatogram.

43 Claims, 10 Drawing Sheets

| Input chromatrogram 46 | | | | | |
|---|---|---|---|---|---|
| Trace 1 48-1 | | Trace 1 Status 50-1 | Trace 2 48-2 | | Trace 2 Status 50-2 |
| Datapoint Number | Intensity | | Datapoint Number | Intensity | |
| 1 | 0 | NP | 1 | 0 | NP |
| 2 | 0 | NP | 2 | 0 | NP |
| 3 | 0 | NP | 3 | 0 | NP |
| 4 | 30 | NP, 6 | 4 | 12 | NP, 6 |
| 5 | 36 | NP | 5 | 24 | NP |
| 6 | 97 | PE | 6 | 78 | PE |
| 7 | 80 | NP | 7 | 54 | NP |
| 8 | 53 | NP | 8 | 28 | NP |
| 9 | 20 | NP | 9 | 12 | NP |
| 10 | 0 | NP | 10 | 0 | NP |

| Output chromatogram 52A | | | | Output chromatogram 52B | | |
|---|---|---|---|---|---|---|
| Datapoint Number | Trace 1A 54A-1 | Trace 2A 54A-2 | | Datapoint Number | Trace 1B 54B-1 | Trace 2B 54B-2 |
| | Intensity | Intensity | | | Intensity | Intensity |
| 1 | 0 | 0 | | 1 | 0 | 0 |
| 2 | 0 | 0 | | 2 | 0 | 0 |
| 3 | 0 | 0 | | 3 | 0 | 0 |
| 4 | 30 | 0 | | 4 | 0 | 12 |
| 5 | 36 | 0 | | 5 | 0 | 24 |
| 6 | 97 | 0 | | 6 | 0 | 78 |
| 7 | 80 | 0 | | 7 | 0 | 54 |
| 8 | 53 | 0 | | 8 | 0 | 28 |
| 9 | 20 | 0 | | 9 | 0 | 12 |
| 10 | 0 | 0 | | 10 | 0 | 0 |

SYSTEMS AND METHODS FOR PROCESSING NUCLEIC ACID CHROMATOGRAMS

FIELD OF THE INVENTION

The field of this invention relates to computer systems and methods for automated processing of nucleic acid chromatograms. Such methods can be used to facilitate the detection and characterization of polymorphisms in heterozygous nucleic acid sequence tracings.

COMPUTER PROGRAM LISTING APPENDIX

One compact disc that includes a Computer Program Listing Appendix has been submitted in duplicate in the present application. The size of the file contained in the Computer Program Listing Appendix, the date of creation, the time of creation, and the file name is found in Table 1 below. In Table 1, the size of the file, in bytes, is provided in column one. Columns two and three respectively represent the date and time of file creation while the fourth column represents the name of the file.

TABLE 1

Contents of the Computer Program Listing Appendix

| Size | Date of Creation | Time of Creation | File Name |
|---|---|---|---|
| 46,000 | Dec. 14, 2003 | 10.27 pm | Splitrace.c |

The Computer Program Listing Appendix disclosed in Table 1, and the contents of the filename contained therein, is hereby incorporated by reference in its entirety.

BACKGROUND OF THE INVENTION

The availability of large amounts of DNA sequence information has begun to influence the practice of biology. As a result of current large-scale sequencing output, analysis methods are not adequate to keep pace with the burgeoning data. To keep up with this growing demand, improved automation is needed, and it is particularly important that human involvement in sequence data processing be significantly reduced or eliminated. Progress in this respect requires both improved accuracy of the data processing software and reliable accuracy measures to reduce the need for human involvement in error correction and make human review more efficient.

At present, DNA sequencing is typically performed using the enzymatic dideoxy chain-termination method of Sanger (Sanger et al. 1977, Proc. Natl. Acad. Sci. 74:5463-5467) in automated sequencers such as the Applied Biosystems (ABI, Norwalk, Conn.) 3730xl DNA Analyzer, the 3730 DNA Analyzer, the ABI PRISM 3100 Genetic Analyzer, the 3100-Avant Capillary DNA sequencer/genotyper, or the 310 Capillary DNA Sequencer/Genotyper. Such sequencers can produce sequence data listing more than one thousand bases. One starts with a DNA template of interest and an oligonucleotide primer complementary to a specific site on the template strand. For each of the four bases (A, G, C, T), a reaction is carried out in which DNA polymerase synthesizes a population of labeled single-stranded fragments of varying lengths, each of which is complementary to a segment of the template strand and extends from the primer to an occurrence of that base. These fragments are then separated according to length by gel electrophoresis, whereupon their relative sizes, together with the identity of the final base of each fragment, allow the base sequence of the template to be inferred.

In automated sequencing (Smith et al. 1986, Nature 321: 674-679), the fragments are labeled with fluorescent dyes attached either to the primer (dye primer chemistry) or to the dideoxy chain-terminating nucleotide (dye terminator chemistry) (Prober et al. 1987, Science 238:336-341). Typically, a different dye is used for each of the four reactions, so that they can be combined and run in a single gel lane (in the case of dye-terminator chemistry, this also allows all four reactions to be carried out in a single tube). For example, one such application employs laser excitation and a cooled CCD (charged coupled device) detector (Kostichka and Smith, U.S. Pat. No. 5,162,654) for the parallel detection of four fluorescently labeled DNA sequencing reactions during their electrophoretic separation in ultrathin (50-100 microns) denaturing polyacrylamide gels (Kostichka et al., Bio/Technology 10:78-81 (1992)). Weiss et al. (U.S. Pat. No. 5,470,710) describes another fluorescence-based sequencing application, using an enzyme linked fluorescence method for the detection of nucleic acid molecules. See also U.S. Pat. No. 6,596,140, which is directed to a multi-channel capillary electrophoresis device and method.

Typically, multiple templates (e.g., 36 or more at a time) are analyzed in separate lanes on the same gel. At the bottom of the gel, a laser excites the fluorescent dyes in the fragments as they pass, and detectors collect the emission intensities at four different wavelengths. The laser and detectors scan the bottom of the gel continuously during electrophoresis in order to build a gel image in which each lane has a ladder-like pattern of bands of four different colors, each band corresponding to the fragments of a particular length.

Computer analysis is then used to convert the gel image to an inferred base sequence (or read) for each template. Typically, this analysis consists of four distinct steps: lane tracking, in which the gel lane boundaries are identified; lane profiling, in which each of the four signals is summed across the lane width to create a profile, or set of "traces", providing a set of four arrays indicating signal intensities at several thousand uniformly spaced time points during the gel run; trace processing, in which signal processing methods are used to deconvolve and smooth the signal estimates, reduce noise, and correct for dye effects on fragment mobility and for long-range electrophoretic trends; and base-calling, in which the processed traces are translated into a sequence of bases.

As used herein, the term "trace" refers to a time-resolved separation pattern obtained by chromatography for a particular compound, such as a nucleotide. This separation pattern is characterized by a plurality of datapoints in which each respective datapoint in the plurality of datapoints represents a signal amplitude at a position in the separation pattern corresponding to the respective datapoint. The value of a given datapoint is determined by a function of an amount of the compound corresponding to the trace that is sensed by the detector at the point in time represented by the datapoint. In typical nucleic acid sequences, for example, the abundance of a base represented by a trace at each datapoint will vary. Datapoints in which the compound represented by the trace is not present, will typically be assigned relatively small signal amplitudes. Conversely, datapoints in which the compound represented by the trace is present, will typically be assigned relatively large signal amplitudes. Thus, a pattern of datapoints having relatively small amplitudes and datapoints having relatively large amplitudes gives rise to "peaks" in the trace. In some embodiments, a trace has more than five datapoints, more than 100 datapoints, or more than 1000 datapoints. In some embodiments, a trace has between two and 100,000 or more datapoints.

Processed traces for nucleic acid sequences are usually displayed in the form of chromatograms consisting of four curves of different colors, each curve representing the signal for one of the four bases and drawn left to right in the direction of increasing time to detection (increasing fragment size). An idealized trace consists of evenly spaced, nonoverlapping peaks, each corresponding to the labeled fragments that terminate at a particular base in the sequenced strand. Thus, for nucleic acids, there will be four traces, with each trace representing a unique nucleotide. Real traces deviate from this ideal for a variety of reasons, including possible imperfections in the sequencing reactions, gel electrophoresis and trace processing. Due to the anomalous migration of very short fragments (caused by relatively greater effects of the dye and specific base sequence on mobility) and unreacted dye—primer or dye—terminator molecules, the first fifty or so peaks of a trace are often noisy and unevenly spaced. Toward the end of the trace, the peaks become progressively less evenly spaced as a result of less accurate trace processing, less resolved as diffusion effects increase and the relative mass difference between successive fragments decreases, and more difficult to distinguish from noise as the number of labeled fragment molecules of a given size decreases. In particular, poorly resolved peaks for the same base may yield a single broad, often lumpy peak.

In better resolved regions of the trace, the most commonly seen electrophoretic anomalies are compressions (Sanger and Coulson 1975, J. Mol. Biol. 94:441-448; Sanger et al., 1977, Proc. Natl. Acad. Sci. 74:5463-5467), which occur when bases near the end of a single-stranded fragment bind to a complementary upstream region, creating a hairpin-like structure that migrates through the gel more rapidly than expected from its length, thus causing a peak to be shifted away from its expected position. This can result in one peak being beneath another, or in two successive peaks for the same base being merged into one. Dye-terminator chemistry appears to resolve most compressions (Lee et al. 1992, Nucleic Acids Res. 20:2471-2483) but this chemistry has its own data quality problems caused by reduced polymerase affinity for the dye-labeled terminal nucleotide.

The goal of base-calling software is to produce a sequence as accurate as possible in the face of the above data problems. As used herein, the term "base-calling" refers to the process of determining the identity of a nucleotide base in a nucleic acid sequence.

Some of the earliest base-calling software was part of the processing software installed on the first ABI sequencing machines (Connell et al., 1987, BioTechniques 5:342-348). That ABI software is often used as a benchmark by which other methods are judged. Although full algorithmic details have not been published, according to an ABI description of its base-calling software (ABI 1996), the program uses mobility curves to predict the peak spacing, and identifies the most likely peak in intervals of the nominal peak spacing, assigning an N in the absence of a good choice. Subsequently, the ABI software adds and removes bases using a criterion involving the uniformity of peak spacing.

The advent of high volume sequencing has prompted development of other base-calling software programs (Giddings et al., 1993, Nucleic Acids Res 21:4530-4540; Golden et al., 1993, in Proceedings of the First International Conference on Intelligent Systems For Molecular Biology, Hunder et al. eds, pp, 136-144, AAAI Press, Menlo Park, Calif.; Golden et al., 1995 in Evolutionary programming IV. Proceedings of the Fourth Annual Conference on Evolutionary Programming, 579-601; Berno, 1996, Genome Research 6:80-91). These programs all perform multiple gel image processing steps including base-calling, and have the merit of allowing efficient centralized processing of the data on a computer independent of the sequencing machine. However, none of these software programs identify heterozygous peaks in traces in a satisfactory manner.

The ABI base-calling software that is available for ABI sequencers can reliably identify approximately half of the available bases. The remaining half typically contains a large number of errors that are either discarded or must be manually corrected by an operator. Work has been done to try and improve upon the accuracy of the ABI base-calling software. For example, Ewing et al., 1998, Genome Res. 8:175-185 describe a base-calling program named phred for automated sequencer traces that achieves a lower error rate than the ABI software. Phred averages between 40 percent to 50 percent fewer errors than the ABI software in test data sets examined independent of position in read, machine running conditions, or sequencing chemistry.

Although the above-identified software programs represent important accomplishments in their own right, they do not satisfactorily base-call heterozygous nucleic acid samples. Each sequencing trace taken from a heterozygous DNA sample (e.g., a human DNA sample) is the product of a sequencing reaction on two physical chromosomes, the maternally derived chromosome and the corresponding paternally derived chromosome. For example, consider the case in which a region of human chromosome IV is to be sequenced. Primers prepared for this sequencing reaction bind to both the maternally derived chromosome IV and the paternally derived chromosome IV. Thus, a mixture of the nucleic acid sequence from the maternally derived and the paternally derived chromosome IV is sequenced. Unlike the case of DNA samples from controlled mouse crosses (where both chromosomes are the same because the parents are inbred), the maternally derived human chromosome IV and the paternally derived human chromosome have points where they differ. That is, there are many heterozygous points (base positions) in the chromosomes where there are different alleles at corresponding positions on the maternally derived and paternally derived chromosomes. At each point where there is heterozygosity between corresponding base positions in the maternally derived and paternally derived chromosomes, two peaks will arise in the trace, one for each of the nucleotides. In humans, approximately one in every 500 to 1000 bases has this heterozygosity. Conventional base-calling software does not satisfactorily identify such double peaks. Rather, such peaks are typically designated as "not read."

The base-calling program TraceTuner (Paracel, Pasadena, Calif.) does have some capability for detecting and recognizing heterozygous bases. However, the heterozygous base recognition algorithms of TraceTuner are unsatisfactory because they require manual intervention. Accordingly, the art still needs improved systems and methods for automatically recognizing heterozygous base pairs in heterozygous nucleic acid samples.

SUMMARY OF THE INVENTION

The present invention addresses the shortcomings of the prior art. Novel systems and methods for detecting polymorphisms in trace sequence data collected from heterozygous samples are disclosed. Using a rule-based system, double peaks in trace sequence data are detected, and each of the peaks in such double peaks are characterized. Information about characterized double peaks is used to create paired homozygous trace sequences from the heterozygous trace sequence data. The paired homozygous trace sequence data can then be base-called using conventional base-calling software such as ABI sequencing software, Phred, or TraceTuner.

The inventive methods and systems are highly advantageous because they allow for the automated sequencing of heterozygous DNA. In this regard, the present invention removes the needs for human interpretation of double peaks in traces. Such human interpretation is prone to error due to its inherently subjective nature. Using the techniques of the present invention, heterozygous traces are automatically converted to a pair of homozygous base traces using a rule-based system.

The techniques of the present invention have wide applicability for genotyping heterozygous nucleic acid samples. For example, one known technique for validating the linkage between a locus in a specific region of genomic DNA to a particular disease trait is to sequence the specific region of DNA from samples taken from each member of a cohort population chosen to study the disease trait. Polymorphisms discovered in this cohort population are then tested (either individually or in the form of a haplotype) to see whether they associate with the disease. The detection of such an association validates the hypothesis that the locus in the subject region of genomic DNA is linked to the disease. The problem with this known technique is that conventional techniques for identifying the polymorphisms necessary to perform the requisite association studies are labor intensive and expensive. Such polymorphisms typically show up as double peaks in sequence traces, and conventional base-calling software has no automated way of reliably sequencing such double peaks. Thus, subjective human intervention is required to characterize such peaks and thereby identify polymorphisms.

The present invention removes the subjective, labor intensive step of identifying polymorphisms. Using the systems and methods of the present invention, heterozygous nucleic acid samples from a cohort population can be automatically sequenced in order to identify single nucleotide polymorphisms (SNPs) or other forms of polymorphisms (markers). Then, each of these SNPs (or other forms of markers) can be tested in association analyses to determine whether the SNP (or other forms of markers) associates with the disease under study. In addition to dramatically reducing the cost of association studies, the systems and methods of the present invention can be used generally in other fields, such as, for example, general SNP discovery, diagnostics, and forensics.

In the specification and claims, reference is made to chromatograms (for example as illustrated in FIGS. 4 and 5) having multiple traces, and having datapoints assigned along the long linear axis of the chromatogram. It should be understood that the chromatogram need not be provided or represented in this form, nor does it need to include four traces combined and aligned in one entity. Thus, a "chromatogram" within the broadest scope of the invention includes, for example, a data file specifying a signal amplitude of a nucleotide measurement associated (or capable of being associated) with a positional indication (i.e., a "datapoint"). The chromatogram may include a plurality of separate files, each specifying the signal amplitudes of one or more nucleotides, which may be combined and normalized to provide a complete set. The signal amplitude is preferably proportional to the concentration of nucleotide detected, but need not be exact.

One embodiment of the present invention provides a method of processing an input nucleic acid chromatogram having a plurality of substantially simultaneous traces. In the method, for each of one or more respective peaks in a first trace in the plurality of traces, a datapoint having a maximum value in the respective peak is marked. Also, for each of one or more respective peaks in a second trace in the plurality of traces, a datapoint having a maximum value of the respective peak is marked. A coordinate is identified in the input nucleic acid chromatogram that is within an overlap threshold number of datapoints of (i) a first datapoint having a maximal value in a first peak in the one or more peaks in the first trace and (ii) a second datapoint having a maximum value in a second peak in the one or more peaks in the second trace. Finally, the first peak is outputted to a first output homogenous representation and the second peak is outputted to a second output homogenous representation. In some embodiments, the overlap threshold number is between two datapoints and seven datapoints and in some embodiments the overlap threshold number is three datapoints.

In some embodiments, the input chromatogram is in an ABI trace file format, a SCF file format, a ZTR file format, or an ALF file format. In some embodiments, the first output homogenous representation and the second output homogenous representation are each written in an ABI trace file format, a SCF file format, a ZTR file format, or an ALF file format. In some instances, when there is more than a threshold number of peaks in the input chromatogram in a predetermined region about the coordinate, the coordinate is not split into separate chromatograms and the first peak and the second peak are each written to the first output homogenous representation and the second output homogenous representation. In some embodiments, the threshold number of peaks is between two peaks and five peaks. In some embodiments the predetermined region is between 2 datapoints and 20 datapoints about the coordinate.

In some embodiments, when a ratio between the first datapoint of the first peak and the second datapoint of the second peak is greater than a threshold ratio value, the first peak and the second peak are each written to the first output homogenous representation and the second output homogenous representation. In some cases, the threshold ratio value is at least 0.2 or at least 0.4. In some embodiments, when a ratio between the first datapoint of the first peak and the second datapoint of the second peak is greater than a threshold ratio value, the first peak and the second peak are each written to the first output homogenous representation and the second output homogenous representation.

In some embodiments, the input nucleic acid chromatogram represents a nucleic acid sequence from a heterozygous nucleic acid sample and the method further comprises scanning the input nucleic chromatogram for a point of insertion or deletion in the heterozygous nucleic acid sample. When a point of insertion or deletion is found, all regions after the insertion or deletion are written to both the first output homogenous representation and the second output homogenous representation. In some instances, the scanning for an insertion or deletion comprises counting a number of peaks that occur in the plurality of traces after a given coordinate. When the number of peaks exceeds an insertion/deletion threshold number, the coordinate is determined to be the point of insertion or deletion in the heterozygous nucleic acid sample. In some embodiments, the insertion/deletion threshold number is between 25 and 75. In other embodiments, the insertion/deletion threshold number is between 75 and 200.

In some embodiments, the method further comprises generating a common peak profile for a plurality of peaks in the input nucleic acid chromatogram, and, prior to outputting to output homogenous representations, checking the first peak or the second peak against the common peak profile. In some embodiments, the common peak profile is generated by (i) determining the average number of datapoints in the peaks in the input nucleic acid chromatogram; and (ii) averaging a profile of all or a portion of the peaks in the input nucleic acid chromatogram that have the average number of datapoints, thereby forming the common peak profile. In some embodiments, the checking comprises determining whether a value of a test datapoint in the first peak or the second peak exceeds, by an error percentage, a value of the datapoint in the common peak profile that corresponds to the test datapoint. In some instances, the error percentage is between about 0.01 and about 0.4. In some instances, the error percentage is about 0.1

Another aspect of the invention provides a computer program product for use in conjunction with a computer system. The computer program product comprises a computer readable storage medium and a computer program mechanism embedded therein. The computer program mechanism is capable of processing an input nucleic acid chromatogram having a plurality of substantially simultaneous traces. The computer program mechanism comprises instructions for marking (A), for each of one or more peaks in a first trace in the plurality of traces, a datapoint having a maximum value in the peak. The computer program mechanism further comprises instructions for marking (B), for each of one or more peaks in a second trace in the plurality of traces, a datapoint having a maximum value of the peak. The computer program mechanism further comprises instructions for identifying a coordinate in the input nucleic acid chromatogram that is within an overlap threshold number of datapoints of (i) a first datapoint having a maximal value in a first peak in the one or more peaks in the first trace and (ii) a second datapoint having a maximum value in a second peak in the one or more peaks in the second trace. The computer program mechanism further comprises instructions for outputting a representation of the first peak to a first output source and a representation of the second peak to a second output source.

Still another aspect of the invention provides a computer system for processing an input nucleic acid chromatogram having a plurality of substantially simultaneous traces, the computer system comprising a central processing unit, and a memory coupled to the central processing unit. The memory stores an input nucleic acid chromatogram and a program module. The program module comprises instructions for marking (A), for each of one or more peaks in a first trace in said plurality of traces, a datapoint having a maximum value in said peak. The program module further comprises instructions for marking (B), for each of one or more peaks in a second trace in the plurality of traces, a datapoint having a maximum value of the peak. The program module further comprises instructions for identifying a coordinate in the input nucleic acid chromatogram that is within an overlap threshold number of datapoints of (i) a first datapoint having a maximal value in a first peak in the one or more peaks in the first trace and (ii) a second datapoint having a maximum value in a second peak in the one or more peaks in the second trace. The program module further comprises instructions for outputting a representation of the first peak to a first output source and a representation of the second peak to a second output source.

Still another aspect of the invention provides a computer program product for use in conjunction with a computer system. The computer program product comprises a computer readable storage medium and a computer program mechanism embedded therein. The computer program mechanism processes an input nucleic acid chromatogram having a plurality of traces. The computer program mechanism comprises a trace split routine. The trace split routine comprises instructions for outputting the first peak from a first trace in the input nucleic acid chromatogram to a first output homogenous representation and a second peak, occurring in a second trace in the input chromatogram at a datapoint that corresponds to the first peak, to a second output homogenous representation. In some embodiments, the second peak corresponds to the first peak when a coordinate in the input nucleic acid chromatogram is within an overlap threshold number of datapoints of a first datapoint having a maximal value in the first peak and (ii) a second datapoint having a maximum value in the second peak. In some embodiments, the overlap threshold number is between two datapoints and seven datapoints.

BRIEF DESCRIPTION OF THE DRAWINGS

Like reference numerals refer to corresponding parts throughout the several views of the drawings.

DETAILED DESCRIPTION OF THE INVENTION

The present invention is directed toward automating the process for sequencing heterozygous nucleic acid sequence chromatograms. A rule-based system is used to interpret such chromatograms. For each input heterozygous chromatogram, two output homogenous representations are created. In cases where a double peak is found in the input chromatogram, the systems and methods of the present invention place one of the peaks in the first homogenous representation and the second peak in the second homogenous representation. In this way, homogenous representations (e.g., two homozygous chromatograms or two homogenous sequences) are automatically created for each input homozygous chromatogram without need for human subjective interpretation. Thus, the methods of the present invention dramatically increase the efficiency by which polymorphisms can be detected in heterozygous nucleic acid tracings. As such, the methods of the present invention have wide applicability in several fields, such as, for example, polymorphism discovery (e.g., single nucleotide polymorphism discovery), association analysis, diagnostics, and forensics.

Figure 1:
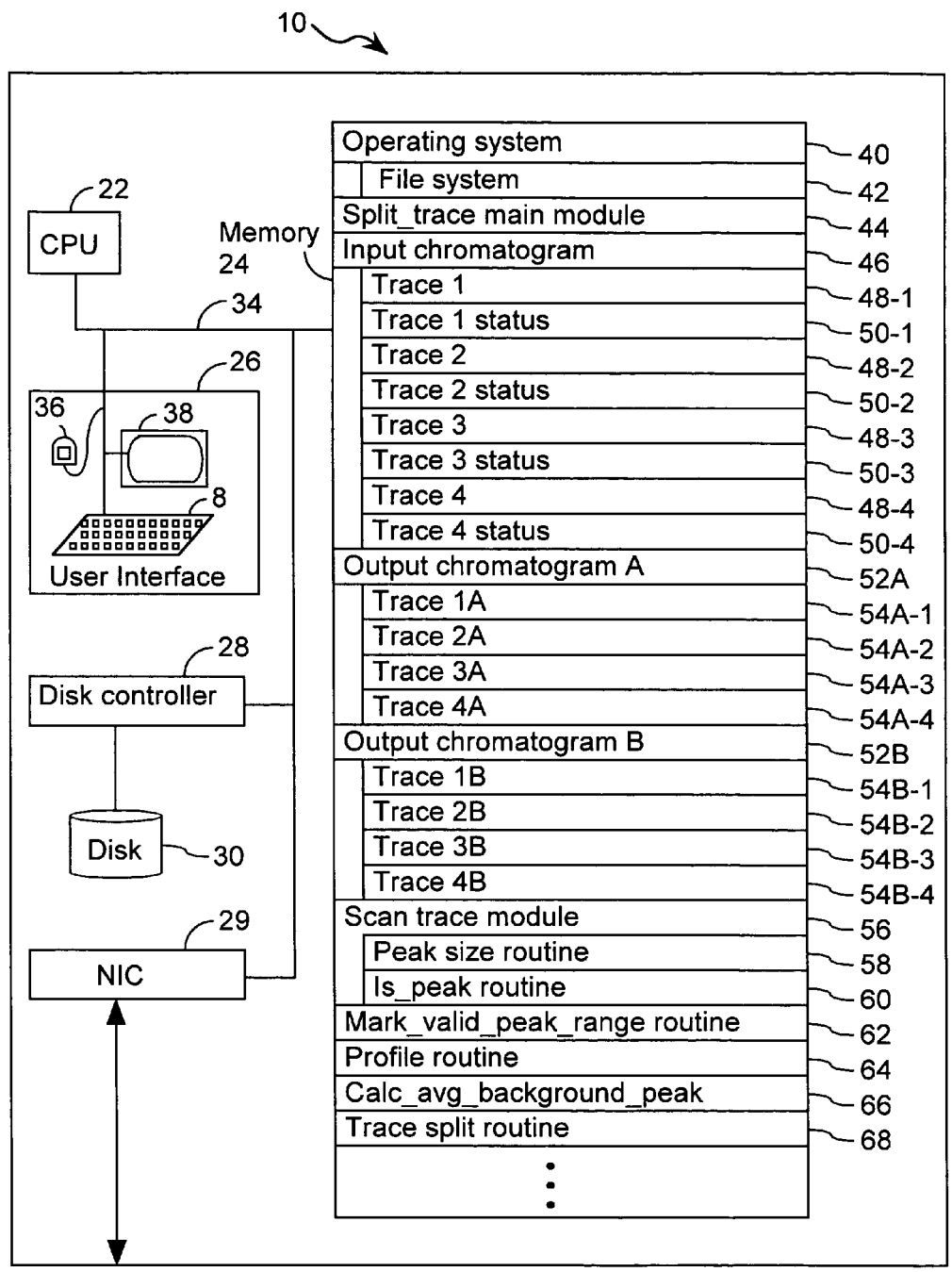
FIG. 1 illustrates a computer system for detecting and characterizing heterozygosity in nucleic acid sequence tracings in accordance with one embodiment of the present invention.
Figure 2A:
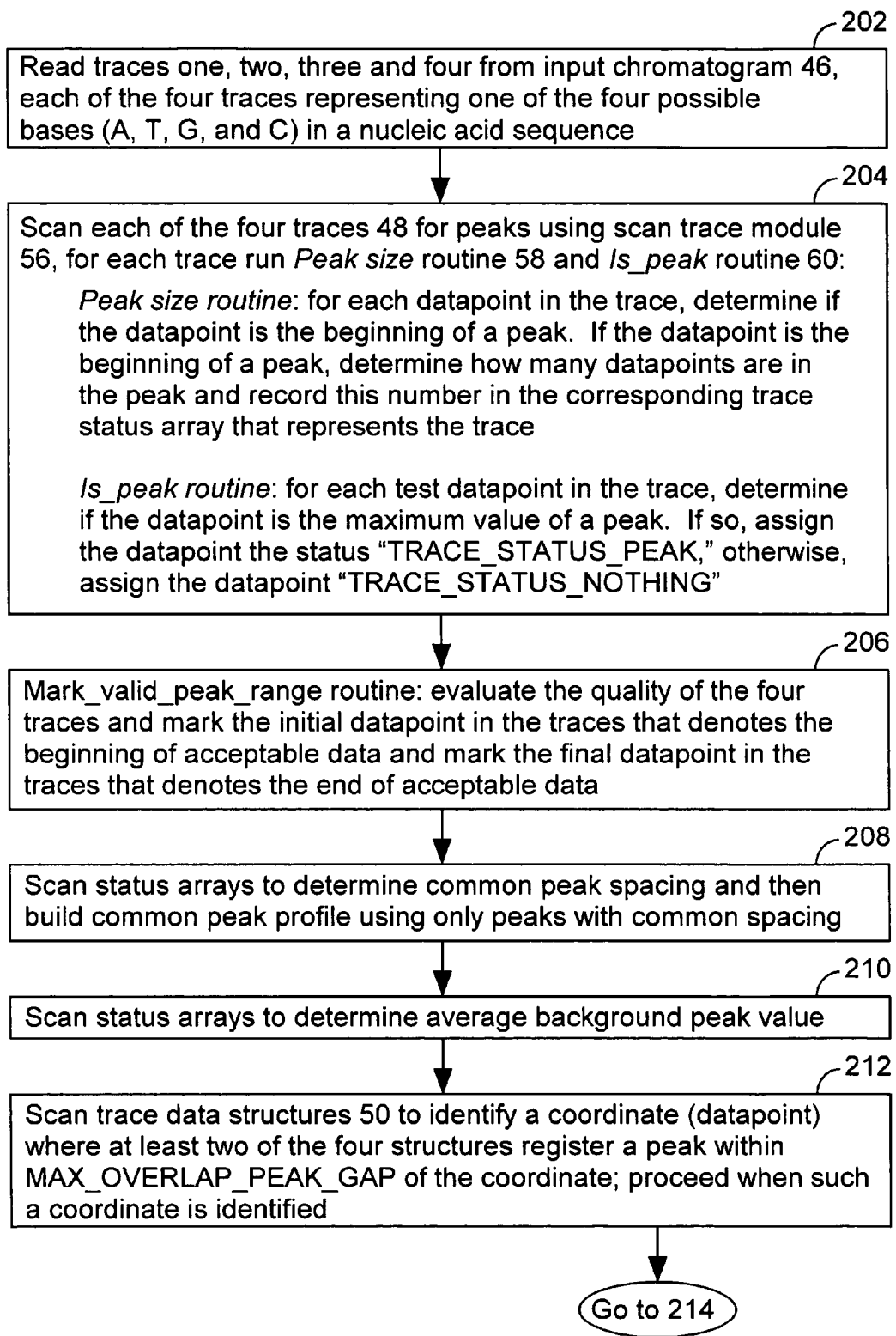
FIGS. 2A-2D illustrate the processing steps for detecting and characterizing heterozygosity in nucleic acid sequence tracings in accordance with one embodiment of the present invention.
Figure 2B:
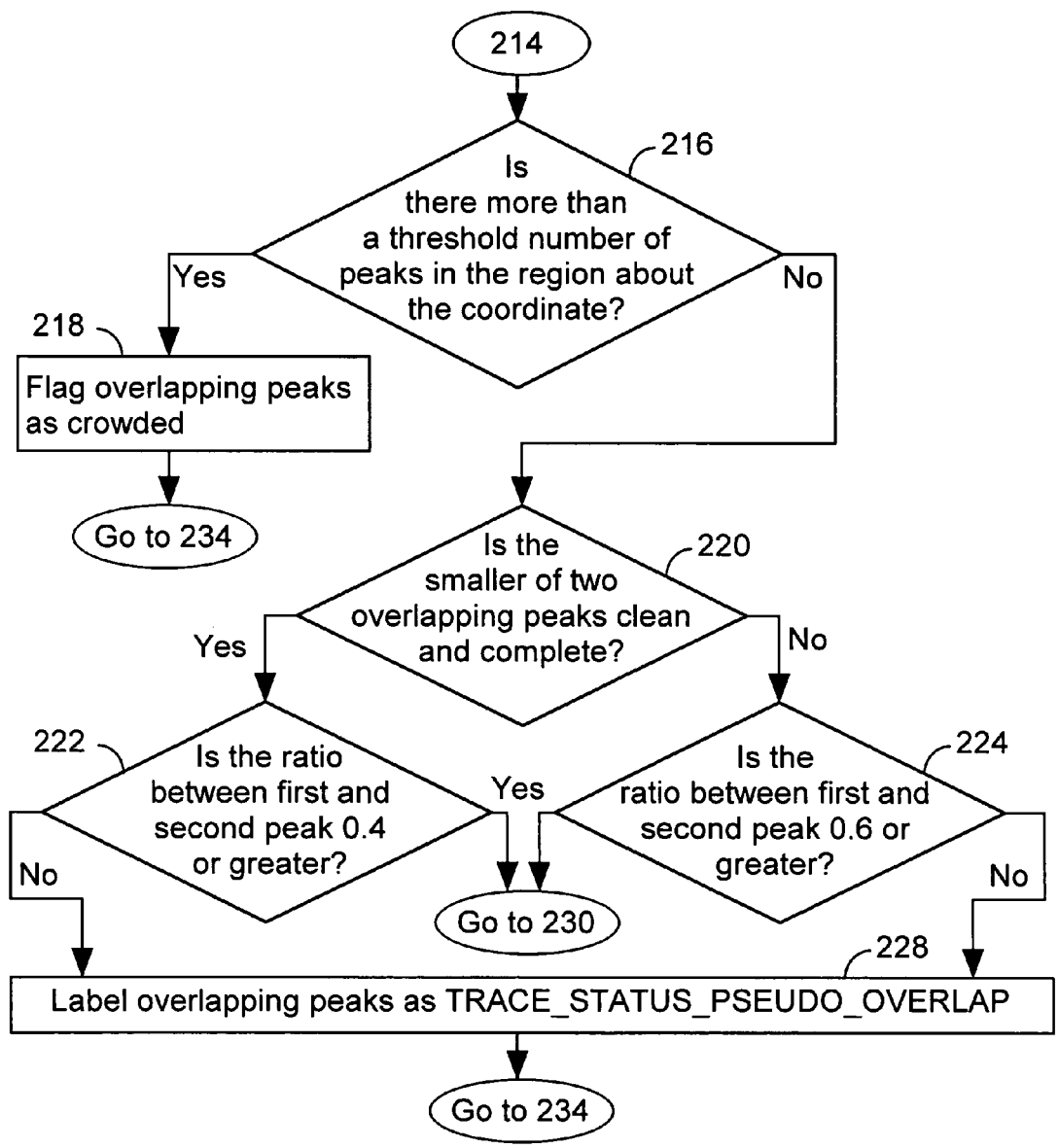
Figure 2C:
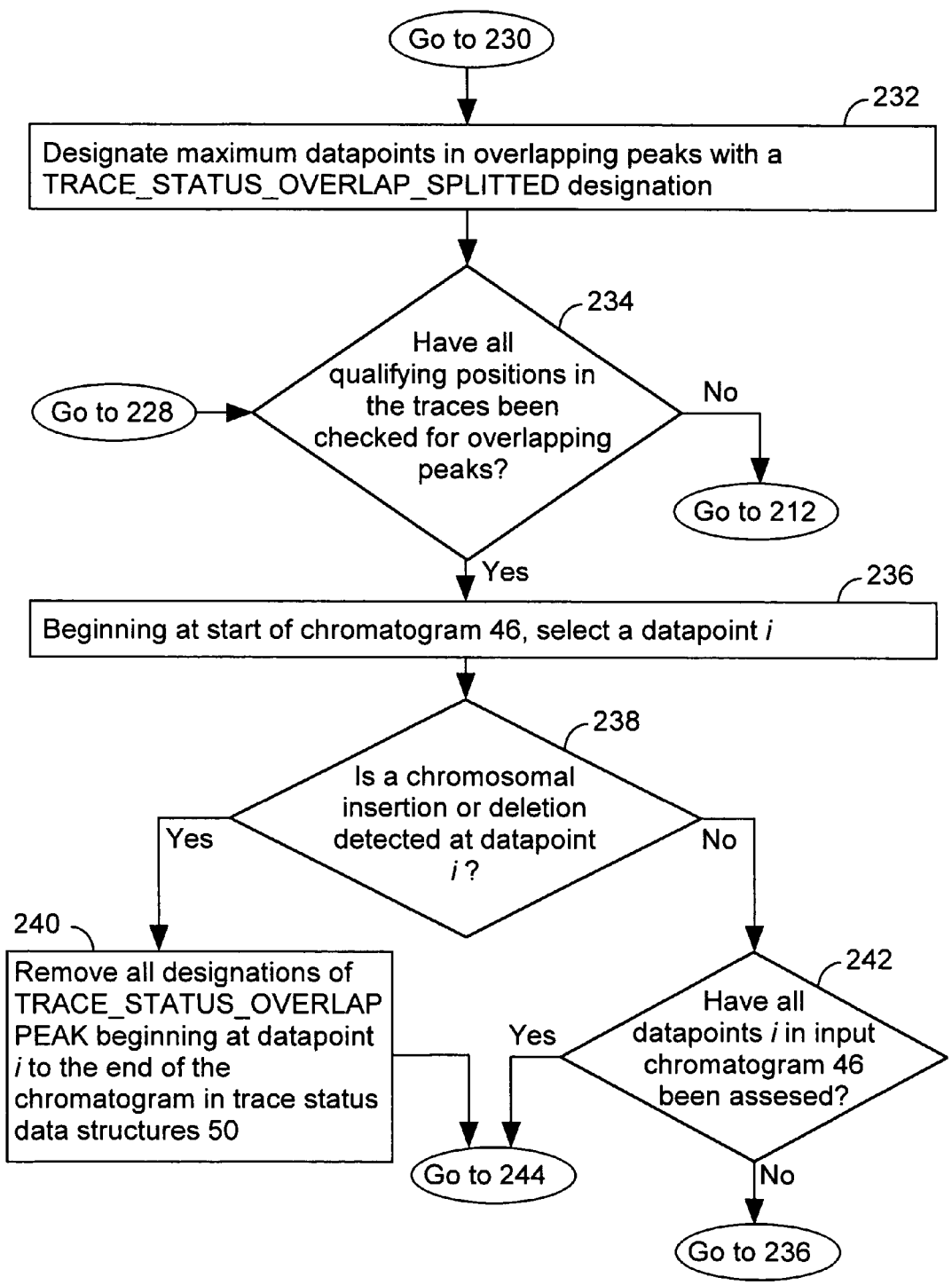
Figure 2D:
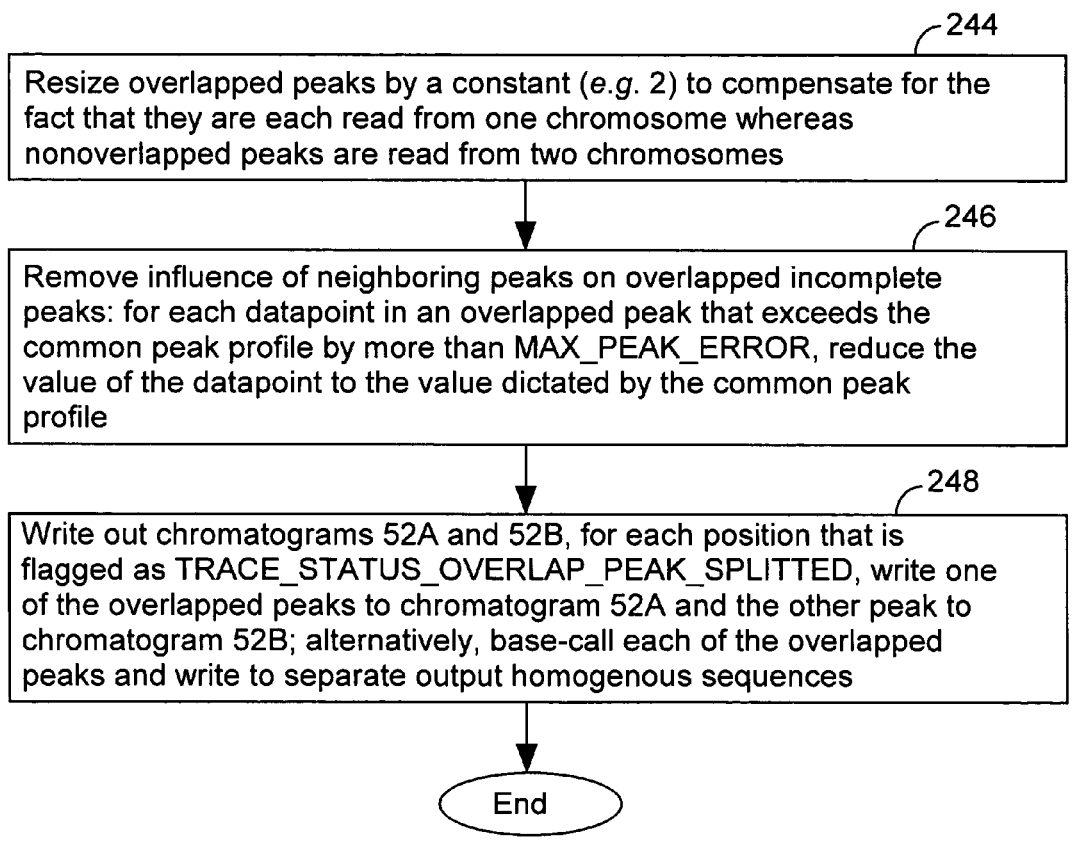

FIG. 1 shows a system 10 for detecting and characterizing polymorphisms in heterozygous nucleic acid sequence chromatograms. System 10 preferably includes:

- a central processing unit 22;
- a main non-volatile storage unit 30, for example a hard disk drive, for storing software and data, the storage unit 30 optionally controlled by storage controller 28;
- a system memory 24, preferably high speed random-access memory (RAM), for storing system control programs, data, and application programs, including programs and data loaded from non-volatile storage unit 28; system memory 24 may also include read-only memory (ROM);
- a user interface 26, including one or more input devices (e.g., keyboard 8, mouse 36) and a display 38 or other output device;
- optionally, a network interface card 39 for connecting to any wired or wireless communication network and/or to a sequencer (not shown); and
- an internal bus 34 for interconnecting the aforementioned elements of the system.

Operation of system 10 is controlled primarily by operating system 40, which is executed by central processing unit 22. Operating system 40 can be stored in system memory 24. In a typical implementation, system memory 24 includes:

- operating system 40;
- file system 42 for controlling access to the various files and data structures used by the present invention; and
- Split_trace main module 44 for splitting a heterozygous input chromatogram 46 into two homozygous output representations (e.g., chromatograms 52A and 52B, respectively).

Split_trace main module 44 reads in input chromatogram 46 and splits it into output homogenous representations (e.g., chromatograms 52A and 52B) using novel methods of the present invention. In general, DNA fragments are labeled with fluorescent dye, and the four different nucleotides are labeled with four different dyes. These labeled DNA fragments are passed through a capillary while a fluorescent detector reads the fluorescent signal along the capillary for each fluorescent dye: at each time coordinate along the capillary, there will be four different fluorescent signal reads, each read corresponding to one of the four possible nucleotides. Thus, input chromatogram 46 includes four arrays of fluorescent signal reads (traces), namely trace 1 (48-1), trace 2 (48-2), trace 3 (48-3), and trace 4 (48-4), where each trace uniquely represents one of the four possible nucleotides (adenosine, thymine, cytosine, guanine).

In the embodiment illustrated in FIG. 1, split_trace main module 44 includes a number of subroutines (submodules). These submodules include scan trace module 56, which scans each of traces 48-1, 48-2, 48-3, and 48-4 and determines the peak positions and peak spacing in each of these traces. Traces 48 include a plurality of datapoints and an intensity value for each such datapoint. Each trace typically consists of several thousand datapoints. For each trace 48, there is a corresponding trace status data structure 50 which stores a status value for each datapoint in the trace represented by the data structure. Split_trace main module 44 further includes mark_valid_peak_range routine 62 for (i) evaluating the quality of the four traces in input chromatogram 46, (ii) marking the initial datapoint in these traces that denotes the start of acceptable data, and (iii) marking the final datapoint in these traces that denotes the end of acceptable data. Split_trace main module 44 further includes profile routine module 64 for building the common peak profile for peaks in each scan. Such profiles are used, for example, to reconstruct the portions of overlapped double peaks that are missing due to overlap with neighboring peaks. Split_trace main module 44 further includes calc_avg_background_peak_routine 66 for calculating the average background in input traces 48 as well as trace split routine 68 for writing out homozygous output homogenous representations (e.g., chromatograms 52A and 52B).

FIG. 2 illustrates a method for splitting a heterozygous input chromatogram 46 into two output homozygous representations (e.g., chromatograms 52A and 52B), in accordance with an exemplary embodiment of the present invention, will be described. In one embodiment of the present invention, the steps depicted in FIG. 2 are performed by split_trace main module 44 in conjunction with various routines called by module 44.

Step 202. In step 202, input chromatogram 46 is read. Input chromatogram 46 can be read from any sequencer that uses four different color dyes or fluorescent tags to distinguish between the four possible bases. Exemplary sequencers include but are not limited to the sequencers listed in Table 2 below.

TABLE 2

Exemplary DNA sequencers

| Company | Model |
|---|---|
| Applied Biosystems (ABI, Norwalk, Connecticut) | 3730, 3730xl DNA Analyzer<br>ABI PRISM 3100 Genetic Analyzer<br>3100-Avant Capillary DNA sequencer/genotyper<br>Capillary DNA Sequencer/Genotype<br>ABI PRISM 377 DNA Sequencer<br>ABI 3700 DNA Sequencer |
| Amersham Pharmacia Biotech (Uppsala, Sweden) | MegaBACE 500, 1000 and 4000; ALF DNA Sequencer |
| Beckman Coulter, Inc. (Fullerton, California) | CEQ 8000, 8800, 2000XL DNA Sequencer system |

Input chromatogram 46 is in any kind of data format that provides chromatogram trace amplitudes. Typically, input chromatogram 46 comprises trace amplitudes, the base calls, their confidence values, and optional textual data about the particular sequencing experiment such as its chemistry, sequencing machine type and operating conditions. A list of common textual data associated with individual trace files is provided at the National Center for Biotechnology Information trace repository (ncbi.nlm.nih.gov/Traces).

In one embodiment, input chromatogram is an ABI trace file, such as a trace file in the ABI 377 file format. For a description of the ABI 377 file format, see "Raw Data File Formats, and the Digital and Analog Raw Data Streams of the ABI PRISM 377 DNA Sequencer," Clark Tibbetts, cs.cmu.edu/~genome/Papers/clark.html. In some embodiments, input chromatogram 46 is in the SCF format. SCF formatted files contain the data for a single reading and include its trace sample points, its called sequence, the positions of the bases relative to the trace sample points, and numerical estimates of the accuracy of each base. The SCF file format is machine-independent, and a version of this file format is described in Dear and Staden, 1992, DNA Sequence 3:107-110.

In some embodiments, input chromatogram 46 is in the ZTR compressed file format. For more information on the ZTR file format, see Bonfield et al., 1995, Nucleic Acids Res. 23:4992-99. In some embodiments, input chromatogram 46 is an ALF formatted file. ALF is a file format developed by Amersham Pharmacia Biotech (Uppsala, Sweden) for storing sequence information from sequencers.

Regardless of the specific file format of input chromatogram 46, each of the four traces within the chromatogram are respectively separated into data structures 48-1, 48-2, 48-3, and 48-4 (FIG. 1). At a minimum, a trace 48 includes a series of datapoints and an amplitude for each datapoint. Ideally, each base in a subject nucleic acid (the nucleic acid that is being sequenced) is represented by a single datapoint in each of the four traces. Datapoints in each of traces 48-1, 48-2, 48-3, and 48-4 are said to correspond if they represent the same base position in a subject nucleic acid sequence. For each datapoint in a given trace 48, there is an indication of the intensity of the dye that corresponds to the given trace 48 at the position represented by the datapoint. In the upper panel of FIG. 3, exemplary data for traces 48-1 and 48-2 include ten corresponding datapoints and their respective intensity values. Each row in the upper panel of FIG. 3A can be considered a datapoint or coordinate of input chromatogram 46.

Figure 3:
FIG. 3 illustrates trace sequence data structures that are created in accordance with one embodiment of the present invention.
Figure 4:
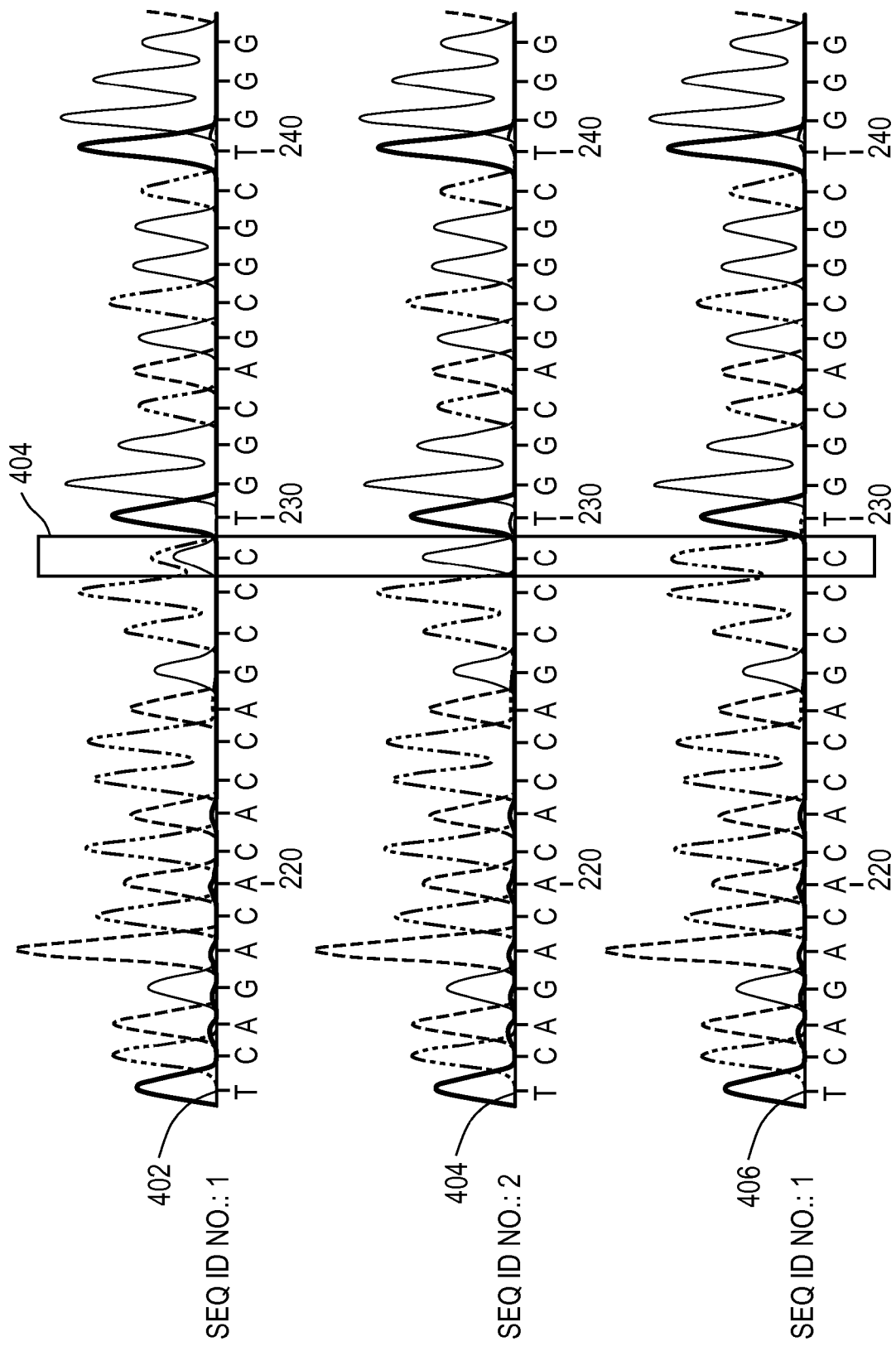
FIG. 4 illustrates an input chromatogram and two exemplary homogenous representations that are created based upon the input chromatogram using the methods of the present invention.

Typically, in cases where the sequenced nucleic acid is either (i) not heterozygous, or (ii) is heterozygous but has been taken from an organism in which the corresponding maternal and paternal chromosomes are identical, only one of the four corresponding datapoints in the traces will register as a "peak". However, as illustrated by datapoint number 6 in the upper panel of FIG. 3, in cases where heterozygous DNA has been sequenced there will be datapoints at which the maternally-derived and paternally-derived chromosome do not have the same base pair, and thus two of the four traces will register a "peak" at the datapoint representing this mismatched base pair. For example, consider the case in which a region on human chromosome 3 is being sequenced. In the case of heterozygous DNA samples, it is possible for arbitrary base position 229 on the maternally-derived chromosome 3 to have the base "G" while the corresponding base position on the paternally-derived chromosome 3 has the base "C". When the base position is sequenced, both the datapoint in the trace that represents the dye for the base "G" and the datapoint in the trace that represents the dye for the base "C" will register a peak. This situation is illustrated in FIG. 4. In chromatogram 402 of FIG. 4, position 229 (box 408) includes a double peak. Thus, when chromatogram 402 is read, datapoint 229 of two different traces 48 will include a peak. The remaining steps in FIG. 2 show how such double peaks can be resolved and split into homozygous "daughter" chromatograms 52 that can then be sequenced on an automated basis without the requirement for subjective human interpretation.

Step 204. In step 204, each of the four traces 48 is scanned using scan trace module 56. Scan trace module 56 includes two routines, peak_size routine 58 and is_peak routine 60. Peak_size routine 58 helps determine the most common peak spacing in each of traces 48. Routine 58 accomplishes this task by evaluating each datapoint in a trace 48 to see if it is the beginning of a peak. If peak_size routine 58 determines that a given datapoint in a trace 48 is the beginning of a peak, then the routine determines how many datapoints are in the peak and this number of datapoints is recorded in the corresponding trace status data structure 50 representing the trace 48. Upper panel of FIG. 3 illustrates. In both traces 48-1 and 48-2, a peak spanning six datapoints begins at datapoint number four. Peak_size routine 58 detects this peak, counts the number of datapoints in the peak, and stores the datapoint peak count in the trace status array 50 uniquely corresponding to the respective traces (trace status arrays 50-1 and 50-2, respectively) at the data element representing datapoint 4 (the beginning of the peak). Information about the most common peak spacing in each trace 48 is subsequently used by the split_trace main module 44 to properly characterize trace 48 and search for double peaks in such traces.

While peak_size routine 58 is directed to determining peak spacing, is_peak routine 60 is directed to precisely identifying the maximum value of each peak, i.e. the peak position or amplitude. Is_peak routine 60 evaluates each datapoint in each of the four traces 48. For each such datapoint, is_peak routine 60 determines if the datapoint is the maximum value of a peak. If so, is_peak routine 60 assigns the datapoint the status "TRACE_STATUS_PEAK." Otherwise, is_peak routine 60 assigns the datapoint the status "TRACE_STATUS_NOTHING." In FIG. 3, is_peak routine 60 has assigned each datapoint in scans 48-1, and 48-2 that is not a peak the value "NP", which is equivalent to TRACE_STATUS_NOTHING, if the datapoint is not a peak. Further, is_peak routine 60 has assigned the peak that occurs at datapoint 6 in traces 48-1 and 48-2 the value "PE", which is equivalent to "TRACE_STATUS_PEAK". These designations are used by split_trace main module 44 in subsequent processing steps.

Step 206. In traces 48 produced by typical sequencers, the quality of the datapoints at the beginning and the end of the traces is typically not reliable. Thus, in step 206, mark_valid_peak_range routine 62 marks the initial point in a given trace 48 where reliable data begins and the final point in the given trace 48 where reliable data ends. In some embodiments, mark_valid_peak_range routine 62 finds the beginning of the valid peak range of a given trace by automatically ignoring an initial predetermined number of datapoints (IGNORE_DATA_INDEX) in the trace. Then, routine 62 looks for the IGNORE_START_PEAK_NUM peak to occur after the initial predetermined number of datapoints have been discarded. For example, if IGNORE_DATA_INDEX is fifty and IGNORE_START_PEAK_NUM is 10, mark_valid_peak_range routine 62 discards the first fifty datapoints and then looks for the tenth peak to occur after the first fifty datapoints are discarded. Routine 62 identifies peaks by looking for the "TRACE_STATUS_PEAK" designation in the appropriate trace status data structure 50. Recall that such peak designations were made by is_peak routine 60 in processing step 204 above. The initial number of datapoints (IGNORE_DATA_INDEX) and peaks (IGNORE_START_PEAK_NUM) that are discarded can be user defined. In one example, between zero and 300 initial datapoints are discarded and between 0 and 25 initial peaks are discarded in order to mark the valid peak start.

The method used to identify the last peak in the valid peak range works much the same way as the process used to identify the initial valid peak. A predetermined number of terminal datapoints in each scan are ignored. Then, routine 62 counts peaks from the terminal end of each scan (excluding the terminal ignored peaks) until a predetermined number of peaks (IGNORE_END_PEAK_NUM) have been discarded. For instance, in the case where IGNORE_DATA_INDEX is fifty and IGNORE_END_PEAK_NUM is ten, the last fifty datapoints are ignored and then the tenth peak from the end of the scan, excluding the last fifty datapoints, is designated as the terminal end of the valid data range. The terminal number of datapoints (IGNORE_DATA_INDEX) and peaks (IGNORE_END_PEAK_NUM) that are discarded in order to find the end of the valid range of a given trace 58 can be user defined. In one example, between zero and 300 final datapoints are discarded and between 0 and 25 final peaks are discarded in order to mark the end of valid peak data.

Step 208. In step 208 profile routine 64 first determines the most common peak spacing for the peaks found in the four traces 48. Here, the term "peak spacing" means the number of datapoints that are in a peak. Thus, the first goal of step 208 is to identify the most common peak spacing for the peaks of traces 48. This is accomplished using the information in status data structures 50. Recall that in step 204, peak size routine 58 identified the peak spacing for each peak in traces 48 and placed this information at the start of each such peak in the corresponding status data structures 50. In step 208, this peak spacing information is reviewed to identify the most common peak spacing. In some embodiments, peaks that are less than a minimum peak space (e.g., 10 datapoints) or greater than a maximum peak space (e.g., 50 datapoints) are ignored when determining the most common peak spacing.

The purpose of finding the most common peak spacing is so that a profile with this most common peak spacing can be created. This profile is used in subsequent processing steps to ensure that single peaks reconstructed from double peaks do not deviate too much from the model profile. Those of skill in the art will appreciate that there are many different ways of developing a model peak profile, and all such methods are within the scope of the present invention. In one embodiment, each peak in the four traces 58 having a peak spacing that is the most common spacing is averaged together to form a model peak profile. In other words, the profile represents a composite of each of the peaks in each of the four traces 48 having the most common peak spacing. In some embodiments, this composite is normalized by dividing each datapoint in the composite peak by max_value, where max_value is the intensity value for the datapoint in the composite peak having the maximum value. Alternatives to such a normalization process are numerous. For example, in some embodiments, the most common peak spacing for each trace 48 is independently determined and a profile is developed for each of the four traces 48 independently. In some embodiments, profiles are developed for not only the most common peak spacing, but also for peak spacings that are slightly smaller or slightly larger than the most common peak spacing. In some embodiments, a check is made to ensure that a peak that is selected for profiling is not overlapped with other peaks and that the peak is not a double peak before it is used to profile a peak. That is, a peak is selected for profiling only in the case where the corresponding datapoints in each of the other traces 48 are not peaks themselves.

Step 210. In step 210, the average background for peaks in input chromatogram 46 is determined. This is done using the following algorithm:

```
100     for each datapoint i in the valid range of datapoints {
102         for each trace 48 {
104             if datapoint i is a peak then {
106                 compare it to the corresponding maximum peak
                    value in each of the other traces 48 and, if a
                    corresponding peak in another trace is larger,
                    add peak i to the average background count
                    and increment the number peaks in the count by
                    one
                }
            }
        }
108     average background count by the number of peaks contributing
        to the background count
```

Essentially, this algorithm works by identifying the datapoints that have been labeled TRACE_STATUS_PEAK (PE) in step 204 above (lines 100 and 102). When such a datapoint (test datapoint) is found in one of the traces 48 (line 104), it is compared to the corresponding peak in each of the remaining traces. If the test datapoint has a value that is less than that of one of the corresponding peaks, the assumption is made that the peak is background and its value is added to the average background count (line 106). In some embodiments, the test datapoint must have a value that is less than the value of a corresponding peak multiplied by the MIN_OVERLAP_PEAK_RATIO, in other words:

test datapoint<(corresponding_peak_in_other_trace*MIN_OVERLAP_RATIO)

where MIN_OVERLAP_RATIO is the minimum ratio between the maximum values of two overlapping peaks that is needed to in order to consider the two peaks to be overlapping as opposed to the case where one of the peaks is merely background and the other peak is the base signal. In some embodiments, the MIN_OVERLAP_PEAK_RATIO is 0.6. This means that if there are overlapping peaks in input chromatogram 46, they will be treated as overlapping if the smaller peak has a maximum value that is at least sixty percent of the maximum value of the larger peak. Otherwise, if this condition is not met, the smaller peak is counted as background in accordance with the algorithm set forth in lines 102 through 108 above.

The algorithm repeats for each datapoint in the allowed range of datapoints. Then, the average background count is divided by the number of background peaks contributing to the average background count to yield the average background count value. In some embodiments, step 210 is performed by calc_avg_background_peak_routine 66.

Step 212. In step 212, trace data structures 50 are scanned in order to identify a coordinate (datapoint) where at least two of the four structures register a peak within MAP_OVERLAP_PEAK_GAP of the coordinate. In other words, an overlapping peak arises when, at roughly the same coordinate along the capillary of the sequencer (in those sequencers that use a capillary), a peak is detected on at least two of the four fluorescent signal scans. Such a coordinate is a candidate for overlapping peaks.

In some embodiments, a first peak in a first scan is considered overlapped with a second peak in a second scan in the input chromatogram 46 when a datapoint having a maximum value in the first peak is within a threshold number of datapoints of the datapoint having a maximum value in the second peak. In other words, step 212 seeks to identify a coordinate in input chromatogram 46 that is within an overlap threshold number of datapoints of (i) a datapoint having a maximal value in a first peak in a first trace 48 in chromatogram 46 and (ii) a datapoint having a maximal value in a second peak in a second trace 48 in chromatogram 46. In a preferred embodiment, this overlap threshold number is three datapoints. That is, the datapoints having maximal values in the first and second peaks must be within three datapoints of each other in the coordinate along the capillary of the sequencer (in those sequencers that use a capillary). In other embodiments, the overlap threshold number is one datapoint, two datapoints, four datapoints, between two datapoints and seven datapoints, eight or more datapoints, or less than 25 datapoints.

Subsequent processing steps test the coordinate identified in this processing step to see if a number of rules are satisfied. If the coordinate does indeed comply with such rules, then the datapoint having the maximum value in each of the two peaks that overlap is labeled as TRACE_STATUS_OVERLAP_PEAK and the two peaks are ultimately spit into separate output chromatogram files 52 or, alternatively, the peaks are base-called and the nucleotide representation of the peaks is written to separate homogenous sequences. In typical embodiments, coordinates in input chromatogram 46 are checked by successive instances of step 212 in a linear fashion, beginning at one end of the allowable datapoints in the chromatogram, in order to see if they contain an overlapping peak. When overlapping peaks are found at a coordinate, process control passes to step 216.

Step 216. In some instances, overlapping peaks are caused artificially when the peaks in input chromatogram 46 are too crowded. Thus, in some embodiments of the present invention, the region around an identified pair of overlapping peaks is checked to determine whether there are too many peaks in the region. In other words, a determination is made as to whether there is more than a threshold number of peaks in input chromatogram 46 in a predetermined region about the coordinate identified in the last instance of step 212. When there are more than a threshold number of such peaks, the overlapping peaks identified in the last instance of step 212 are not split and they are ultimately written to both output homogenous representations.

Two parameters are typically used in processing step 216: (i) a window size and (ii) a maximum number of peaks that are allowed in the window size. For example, consider the case in which the window size is seven and the maximum number of peaks allowed in this window is three. In step 216, the coordinate selected in the last instance of step 212 and the three datapoints preceding and the three datapoints following this coordinate are checked in all four traces 48 (for a total of 7×4=28 datapoints) and the number of peaks in these regions is summed. If the number of peaks exceeds 3 (216—Yes), then process control passes to step 218 where each peak in the examined region is flagged as crowded and the peaks in this region are not separated into different output homogenous representations. If the number of peaks in the region is three or less (216—No), then the peaks are not flagged as crowded.

It will be appreciated that different window sizes and maximum allowable peak threshold in such window sizes can be used. In some embodiments, the window size examined in step 216 is between 4 and 8 datapoints, between 5 and 10 datapoints, between 2 and 20 datapoints, more than 20 datapoints or less than 50 datapoints. In some embodiments, the maximum allowable number of peaks in the window applied in step 216 is two peaks, three peaks, four peaks, five peaks, between two peaks and five peaks, between five peaks and ten peaks, more than ten peaks, or less than 50 peaks.

Step 218. Process control passes to step 218 when a determination is made that the overlapping peaks identified in the last instance of step 212 lie in a region of the chromatogram 46 in which the peaks are too crowded together. Thus, in order to prevent a false positive measurement, such peaks are flagged as crowded and are no longer considered peaks. The intensities in such crowded regions are written to both output homogenous representations (e.g., chromatograms 52A and 52B). Once crowded peaks have been flagged as crowded, process control passes to step 234 below.

Steps 220-224. Although DNA from each of the two chromosomes in heterozygous DNA samples should be equal, the maximum values of overlapping peaks are not always the same. Many factors affect maximum peak values such as dye amount, neighboring interference, etc. Therefore, there is some allowance for overlapping peaks to have different amplitudes. In some embodiments, the amount of allowance tolerated depends on whether the smaller of the two overlapping peaks is clean and complete. If the smaller peak is clean and complete (220—Yes), then the ratio between the first (smaller) peak and second (larger) peak can be as small as 0.2 in one embodiment of the invention (step 222). In some embodiments, the minimum allowable ratio when the smaller peak is clean and complete is between 0.1 and 0.95. In more preferred embodiments, the minimum allowable ratio is at least 0.2 or at least 0.4.

If the smaller of the two overlapping peaks is not clean and complete (220—No) then the ratio between the first and second peaks can only be as small as 0.6 in one embodiment of the invention (Step 224). In some embodiments, the minimum allowable ratio when the smaller peak is not clean and complete is between 0.1 and 0.95. In more preferred embodiments, the minimum allowable ratio is at least 0.2. In still more preferred embodiments, the minimum allowable ratio is between about 0.2 and about 0.6.

Step 228. If the overlapping peaks fail to satisfy conditions 220 through 224 (222—No or 224—No) then process control passes to step 228 where the peaks are labeled as pseudo overlapping peaks. Pseudo overlapping peaks are written to each of the homogenous representations (e.g., output chromatograms 52) in subsequent processing steps rather than being split into separate chromatograms. Once the peaks have been flagged as pseudo overlapping, process control passes to step 234 below.

Step 232. If the overlapping peaks do satisfy conditions 220 through 224 (222—Yes or 224—Yes) then process control passes to step 232 where the peaks are labeled as overlapping peaks (TRACE_STATUS_OVERLAP_SPLITTED). Overlapping peaks are written to separate chromatograms 52 in subsequent processing steps. In some embodiments, the overlapping peaks must satisfy additional rules in order to be designated as overlapping peaks. For example, in some embodiments, the smaller of the two peaks must be larger than some threshold background level in order for the overlapping peaks to be designated as overlapping. If the smaller of the two peaks does not satisfy this requirement, then the peaks are labeled as pseudo overlapping peaks and they are not split into separate output homogenous representations (e.g., chromatogram files 52).

Step 234. In step 234, a determination is made as to whether the complete valid region of the input chromatogram 46 has been checked for overlapping peaks. If not (234—No), process control passes back to step 212 in order to find another coordinate in which there are candidate overlapping peaks. Then, steps 216 through 234 are repeated for the new candidate overlapping peaks in order to determine whether to label the candidate overlapping peaks as crowded peaks (peaks are too crowded), pseudo overlapping (peaks do not satisfy ratio or background requirements) or overlapping peaks. Typically, successive instances of step 212 retrieve the coordinates of overlapping peaks from input chromatogram 46 in a linear order, progressing from one end of the chromatogram to the other, until all valid datapoints have been tested. However, the present invention is not limited to such an approach and in fact, any approach to obtaining overlapping datapoints in successive instances of step 212 can be followed so long as all or a portion of the overlapping peaks are tested with steps 216 through 234.

Figure 5:
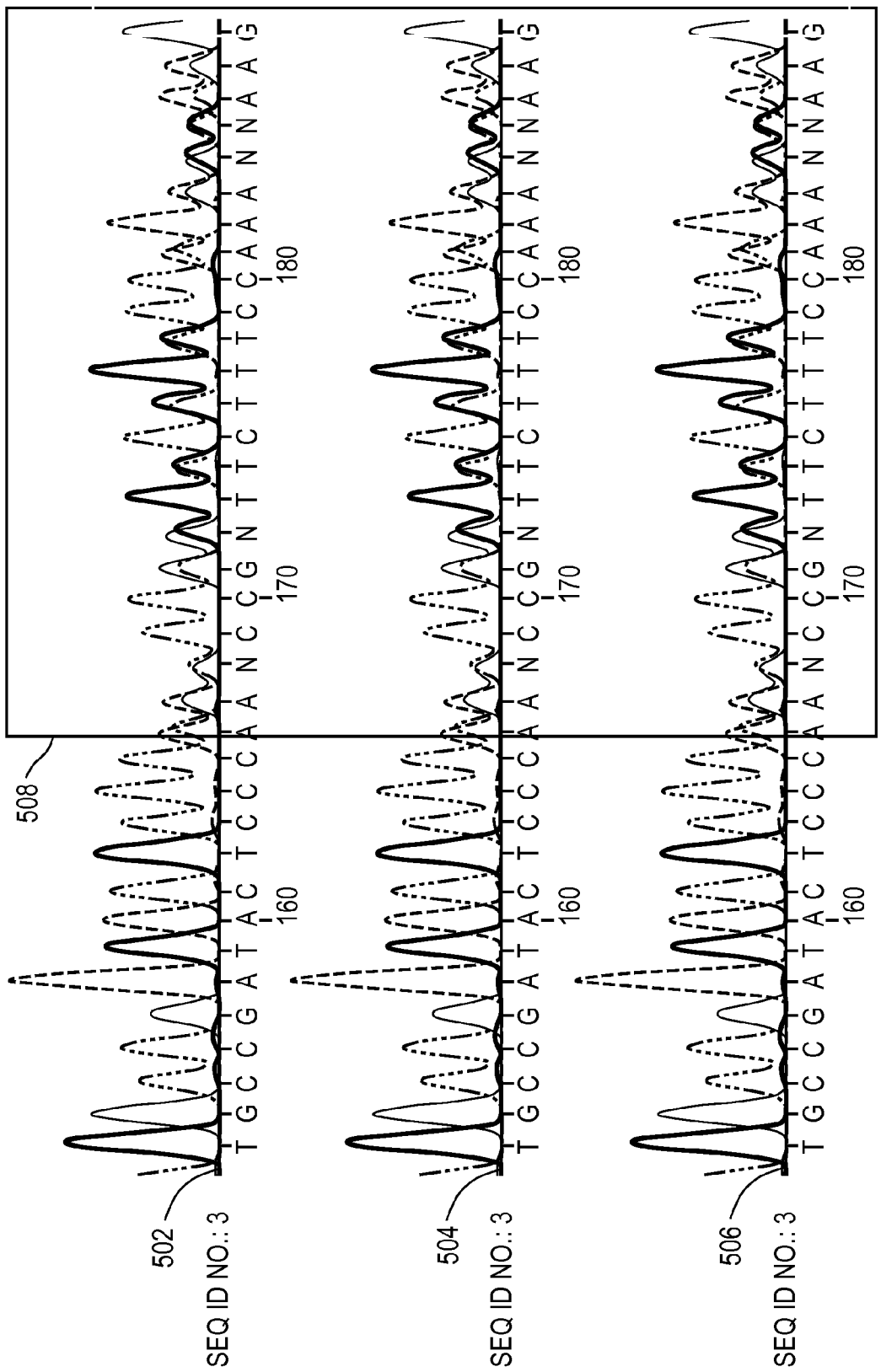
FIG. 5 illustrates an input chromatogram and two exemplary homogenous representations that are created based upon the input chromatogram using the methods of the present invention.

Step 236. Once all candidate overlapping peaks have been labeled as pseudo overlapping, crowded, or overlapping (234—Yes), a new loop through input chromatogram 46 is performed in order to determine whether there is an insertion or deletion. Traces 48 will have numerous peaks marked as pseudo overlapping or overlapping beginning at the coordinate where a deletion or insertion begins in one of the two chromosomes. Furthermore, because the chromosomes will no longer align after the point of insertion or deletion, there will be more peaks in traces 48 then would be typically found if corresponding chromosomes were properly aligned. This situation is illustrated in FIG. 5. In FIG. 5, an insertion appears at coordinate 166 of the heterozygous nucleic acid that is being sequenced. Thus, from coordinate 166 on, there are numerous peaks in the input chromatogram (box 508).

In step 236, a datapoint i in chromatogram 46 is selected and subsequently tested in processing step 238.

Step 238. Step 238 checks to make sure that the coordinate identified in the last instance of step 236 is not in fact the beginning of an insertion or a deletion in one of the two corresponding chromosomes in a heterozygous nucleic acid sample. In one embodiment of the present invention, the insertion/deletion check is accomplished using two different tests. In the first test, a determination is made as to whether the number of peaks that remain in the input chromatogram 46 (or in a certain region of the input chromatogram 46) beginning at the coordinate (datapoint) i selected in the last instance of step 236 exceeds a threshold number peaks. If so (238—Yes), process control passes to step 240 where each peak that follows datapoint i is marked as an unoverlapped peak. In some embodiments, the threshold number of peaks that is permissible in the remainder of an input chromatogram 46 is between 25 and 75, between 50 and 100, between 75 and 200, between 150 and 400, or greater than 500.

The second test that is used to detect insertions and deletions in a heterozygous nucleic acid sample considers the type of peaks that are found in the remainder of the input chromatogram 46 (or some window of the input chromatogram following the datapoint i identified in the last instance of step 236). If the percentage of the total number peaks in the remainder of the input chromatogram 46 that is overlapping (or pseudooverlapping) exceeds a threshold percentage (238—Yes) then process control passes to step 240. In some embodiments, this threshold percentage is between two percent and ninety percent. In more preferred embodiments, this threshold percentage is between ten percent and fifty percent. In still other embodiments, this threshold percentage is between twenty percent and forty percent. In one preferred embodiment, the threshold percentage is twenty-five percent.

Step 240. Process control passes to step 240 when a chromosomal insertion or deletion is detected at a coordinate (datapoint) i in input chromatogram 46. When this is the case, each set of overlapped peaks that had been previously identified as overlapping is marked as nonoverlapping peaks in step 240. This is done so that all data in the input chromatogram, from the point where a deletion or insertion is first detected, is written to both chromatogram files 52A and 52B. In some embodiments of the present invention, deletions or insertions are identified and flagged. Then, an attempt is made to realign the chromosomes after the insertions and/or deletions are accounted for and flag overlapping peaks in the realigned sequences using the techniques outlined, in FIG. 2.

Step 242. If a chromosomal insertion or deletion is not detected at datapoint i (238—No), a determination is made as to whether all datapoints i in input chromatogram 46 have been assessed (step 242). If so (242—Yes), process control passes on to step 244. If not (242—No), process control passes back to step 236 where, typically, the next successive datapoint i in the input chromatogram 46 is selected.

Step 244. In the case of heterozygous nucleic acid samples, the detected signal is contributed to by DNA from both chromosomes, so homozygous (overlapping) peaks normally have higher values than heterozygous peaks. Step 244 corrects for this phenomenon by multiplying each homozygous peak (each peak that is marked as overlapping) by a constant. Typically this constant is the factor two. In some embodiments the constant is in the range between about 1.1 and about 3.2.

Step 246. The influence of neighboring peaks on overlapped incomplete peaks is accounted for in step 246. For each datapoint in an overlapped peak that exceeds the common peak profile that was modeled in step 208 (FIG. 2A) by more than MAX_PEAK_ERROR, the value of the datapoint is reduced to the value dictated by the common peak profile. In preferred embodiments, MAX_PEAK_ERROR is 0.1. In some embodiments, MAX_PEAK_ERROR ranges between 0.01 to 0.4. Thus, step 246 has the effect of correcting overlapping peaks in traces 48 by ensuring that their profiles do not deviate by too much from the common peak profile developed in step 208.

Step 248. In step 248, chromatograms 52A and 52B are generated. For each position that is flagged as TRACE_STATUS_OVERLAP_PEAK_SPLITTED (that is, each peak that successfully remains flagged as overlapping), one of the overlapping peaks is written to one of chromatograms 52A and 52B and the other of the overlapping peaks is written to the other of chromatograms 52A and 52B by trace split routine 68. In some embodiments, chromatograms 52A and 52B are generated in an ABI trace file format, a SCF file format, a ZTR file format, or an ALF file format.

FIG. 3 illustrates step 248. In the upper panel of FIG. 3, it is apparent that there is an overlapping peak centered at coordinate 6 in traces 48-1 and 48-2. Assuming that these peaks satisfy the tests put forth in FIG. 2 and become labeled as overlapping, they will be split into two different output homogenous representations (e.g. chromatograms 54). Exemplary output homogenous representations, output chromatograms 52 are illustrated in the lower panel of FIG. 3. In the lower panel, output chromatogram 52A receives the peak from trace 48-1 but not the peak from trace 48-2. Correspondingly, output chromatogram 52B receives the peak from trace 48-2 but not the peak from trace 48-1.

Example 1

The processing techniques in accordance with one embodiment of the present invention have now been disclosed. Referring to FIG. 4, a graphic illustration of the techniques of the present invention is provided. In FIG. 4, there is an input chromatogram 402 that includes a double peak at position 229 (box 408). Conventional base-calling software has identified this double peak as cytosine (C). However, applying the inventive methods of the present invention to input chromatogram 402 yields output chromatograms 404 and 406 in which the double peak at position 229 has been split into two homozygous peaks, one for each of output chromatograms 404 and 406. Upon reading output chromatograms 404 and 406, the conventional base-calling software correctly identifies that coordinate 229 consists of a guanine (chromatogram 404; G) and a cytosine (chromatogram 406; C).

Typically, the input chromatogram 402 contains more than one double peak. For example, consider the case in which the input chromatogram is based upon a heterozygous nucleic acid sample that includes the sequences:

AC<u>G</u>TTT<u>C</u>
and

AC<u>C</u>TT<u>A</u>C

Together, these sequences can be represented with the notation AC(G/C)TT(T/A)C, where (G/C) represents a first double peak and (T/A) represents a second double peak in the chromatogram 402 corresponding to the input sequence. In such instances, the methods of the present invention will output one of the two possible homozygous representations of the heterozygous input:

(I)         ACGTTTC and ACCTTAC,
    or
    (II)        ACCTTTC and ACGTTAC.

In other words, the systems and methods of the present invention are not designed to determine the "true" sequence of the heterozygous sample which, in the example presented above, is sequence pair (I). Rather, the intent of the systems and methods of the present invention is to generate homozygous representations of heterozygous input data so that polymorphisms in the heterozygous data can be discovered in an automated fashion. The homozygous representations can be in the form of, for example, homozygous sequences or homozygous chromatograms. In preferred embodiments, the homozygous representations are in the form of homozygous chromatograms so that sophisticated base-calling techniques can be applied to the representations.

Example 2

Figure 6:
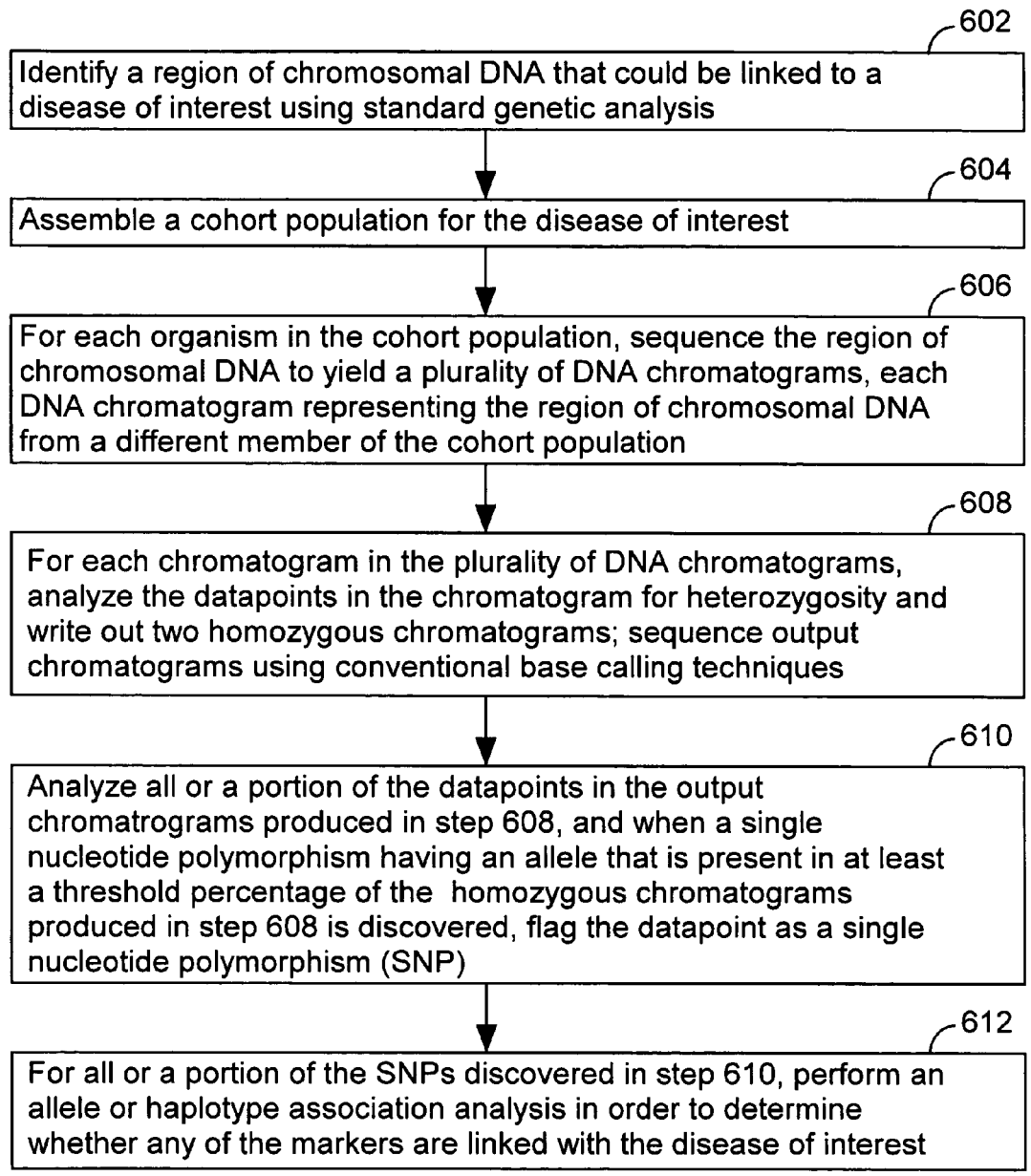
FIG. 6 illustrates an application that uses the processing steps of FIG. 2 to validate the association of a locus with a disease of interest.

Identification of genetic susceptibility factors for complex human diseases can generate insight into their pathogenesis, and novel strategies for disease treatment and prevention. Despite considerable effort, genetic variants accounting for susceptibility to most of the common diseases in the human population have yet to be identified. One reason for this paucity of information is the amount of time and labor involved in validating linkages between genetic loci and diseases. One of the rate-limiting tasks in such validation strategies is the identification of markers in suspected loci. Referring to FIG. 6, the present invention uses the automated method of splitting a heterozygous input chromatogram 46 into homozygous output chromatograms (e.g., the method depicted in FIG. 2) to significantly lower the time and expense of identifying markers. In the application described in FIG. 6, a region of chromosomal DNA (a locus) is analyzed to determine whether the locus is linked to a disease or trait of interest.

Step 602. In step 602, a region of chromosomal DNA (loci) that could be linked to a trait of interest is identified using standard genetic analysis. Exemplary traits of interests are described below in the section entitled "exemplary traits." In one approach, classic Mendelian analysis is used to identify specific genes that are linked to traits of interest. In a Mendelian approach, individual phenotypes that are highly informative of the underlying genotype are used to characterize genes. In situations where the phenotype (trait under study) provides very little information on the underlying genotype, quantitative genetics can be used to discover a linkage between a loci (termed a quantitative trait loci) and a trait under study. Quantitative genetics approaches require the construction of a genetic map for a species under study. A genetic map shows the ordering of loci along a chromosome and the relative distances between them. Such maps can be constructed using regression analysis (Soller et al., 1976, Theor. Appl. Genet. 47:35-39) or interval methods (Lander and Botstein, 1989, Genetics 121:185-199). Markers that can be used in such maps include, but are not limited to, single nucleotide polymorphisms, restriction fragment length polymorphisms, microsatellite markers, short tandem repeats, sequence length polymorphisms, and DNA methylation. Once a genetic map has been constructed, loci that link to traits of interest can be discovered using (i) linear models such as a t-test (e.g., Sokal and Rohlf, 1995, Biometry 2$^{nd}$ Ed., W. H. Freeman and Co., NY), ANOVA or regression, or (ii) or maximum likelihood (e.g., Genetics and Analysis of Quantitative Traits, Lynch and Walsh, 1998, Sinauer Associates, Inc., Sunderland, Mass., Appendix 4).

Family studies have clearly demonstrated a heritable predisposition to many common human diseases such as asthma, autism, schizophrenia, multiple sclerosis, systemic lupus erythematosus, and type I and type II diabetes mellitus. For a review, see Risch (2000) Nature 405:847-56. Over the last 20 years, causative genetic mutations for a number of highly penetrant, single gene (Mendelian) disorders such as cystic fibrosis, Huntington's disease and Duchene muscular dystrophy have been identified by linkage analysis and positional cloning in human populations. These successes have occurred in relatively rare disorders in which there is a strong association between the genetic composition of a genome of a species (genotype) and one or more physical characteristics exhibited by the species (phenotype). To some extent, the same methods have been used to identify genetic variants associated with susceptibility to common diseases in the general population. For a review, see Lander et al. (1994) Science 265:2037-48. Genetic variants associated with susceptibility to subsets of some common diseases such as breast cancer (BRCA-1 and -2), colon cancer (FAP and HNPCC), Alzheimer's disease (APP) and type II diabetes (MODY-1, -2, -3) have been identified by these methods. In some instances, multiple chromosomal regions that could be linked to a trait under study are identified in step 602 and each of these regions are either analyzed concurrently or individually using the subsequent processing steps illustrated in FIG. 6.

For methods on identifying loci that are linked to a trait of interest, see: Risch (2000) Nature 405:847-56; Lander et al. (1994) Science 265:2037-48; Nadeau and Frankel, 2000, Nature Genetics 25:381-84; Fisch et al., 1996, Genetics 143: 571-77, Luo et al. 1992, Heredity 69:236-242, Jiang et al., 1997, Genetics 101:47-58, Olson et al., 1999, Statist. Med. 18:2961-81, Schork et al., 1998, and TIG 14:266-72, Haines and Pereicak-Vance, Approaches to Gene Mapping in Complex Human Diseases, Wiley-Liss, Inc.

Step 604. Once a loci that may be linked to a trait under study has been identified, a cohort population is assembled. Ideally, the cohort population includes members that differentially exhibit the trait under study. For example, if the trait under study is breast cancer, a typical cohort population will include females that have breast cancer and females that do not have breast cancer. In Cheng et al., 1999, Genome Res 9:936-949, a composite cohort of 142 unrelated Caucasians for whom angiograms had been quantitated and scored by the Gensini method (Gensini, 1975, Coronary arteriography, Futura Publishing Co., New York, N.Y.) was used. These scores were used to subdivide the cohort into quintiles that represented differing severities of coronary arterial occlusion.

Step 606. In step 606, the cohort population is genotyped. Typically, this involves sequencing the region or regions of chromosomal DNA identified in step 602 in each member of the cohort population in order to yield a plurality of DNA sequences. In some instances, DNA from cohort members is obtained from blood using standard techniques such as the method of Bell et al., 1981, Proc. Natl. Acad. Sci. 78:5759-63 or using a DNA isolation kit (e.g., the Puregene DNA Isolation Kit, Gentra Systems, Inc., Minneapolis, Minn.). Purified DNA is amplified using primers specific to the region or regions identified in step 602 and amplified regions are sequenced using a sequencer, such as any one of the sequencers disclosed in Table 2, above. Step 606 results in the generation of a plurality of DNA sequences, each DNA sequence representing the region of chromosomal DNA identified in step 602 from a different member of the cohort population. In situations where multiple regions of chromosomal DNA were identified, step 606 results in multiple sequences for each member of the cohort population, one sequence for each of the regions identified in step 602. Each such sequence is represented by a nucleic acid chromatogram 46 that is generated by the sequence.

Step 608. The sequencing of the plurality of chromatograms generated by sequencers in step 608 represents one of the most time-consuming steps of the method illustrated in FIG. 6 when conventional base-calling software is used to sequence such sequences, particularly in the case where the source of nucleic acid is heterozygous. Using conventional base-calling software, each point of heterozygosity in a chromatogram 46 must be visually inspected to see which two bases are present. Not only is this time consuming, it is exposed to subjective human interpretation. Advantageously, the present invention circumvents this subjective time-consuming step by automatically splitting heterozygous chromatograms 46 into homozygous chromatograms 52 using the techniques depicted in FIG. 2. Homozygous chromatograms 52 can then be sequenced using conventional base-calling software in order to sequence the nucleic acids amplified and/or sequenced in step 606.

Step 610. In one embodiment of step 610, all or a portion of the datapoints in output chromatograms 54 are analyzed for single nucleotide polymorphisms (SNPs). A single nucleotide polymorphism (SNP) arises when there are different alleles at a given datapoint. For example, consider the case in which a given locus in ten members of the cohort population is sequenced. Consider a locus including datapoint 90, corresponding to a given base in the cohort population. If the base at position 90 varies in the ten sequences corresponding to the ten members of the population, position 90 is defined as a SNP. For example, if a heterozygous nucleic acid is considered, the ten cohort members will yield one maternal-based sequence and one paternal-based sequence, for a total of twenty sequences. If more than one nucleic acid is represented in position 90 in the twenty sequences, the position is considered to be a SNP. In some embodiments, a more rigid criterion is used: the minor allele must be present in more then one of the sequences. Thus, under this more rigid criterion a result in which 19 of the 20 sequences code for guanine and 1 codes for adenosine would not be considered a SNP. However, a result in which 18 of the sequences code for guanine and 2 code for adenosine would be considered a SNP. Here, guanine is the major allele and adenosine is the minor allele. In still other embodiments, the minor allele must be in at least about five percent of the DNA samples that have been sequenced, at least about ten percent of the DNA samples that have been sequenced, at least about fifteen percent of the DNA samples that have been sequenced, or more than about twenty percent of the DNA samples that have been sequenced.

Step 612. The association of a region of chromosomal DNA (locus) with a trait under study is considered validated if a marker or a haplotype within the locus associates with the trait. In step 612, each marker (e.g., SNP) discovered in step 610, or haplotypes derived from such markers, are tested for association with the trait under study using association analysis. The goal is to identify a marker or a haplotype that is overrepresented in a portion of a cohort population that represents one phenotype of the trait under study. For example, in Campbell et al., 1999, Mol. Psychiatry 4:68-70, a cohort of 170 female Caucasian anorexia nervosa sufferers and 150 normal female controls were genotyped. An association analysis of markers in this cohort population revealed that a particular allele of the marker D11S911 was significantly over-represented in the anorexia nervosa population. A statistical test such as a chi-square test or Fisher's two-tailed exact test (Sokal and Rohlf, 1995, *Biometry*, $3^{rd}$ ed., Freeman, San Francisco, Calif.) can be used to determine whether an allele of a marker in the locus or a haplotype in the locus associates with a particular phenotype of the trait under study.

Haplotypes can be constructed using the marker information that is identified in step 610 using conventional techniques. Such techniques include, but are not limited to those disclosed in Stephens et al. 2001, *Am. J. Hum. Genet.* 68:978-89, Liu et al., 2001, Genome Res. 11:1716-1724, Abescasis et al. 2002, Nature Genet. 30:97-101. In addition, the software analysis package Hapscope supports computational haplotype construction using an expectation-maximation or Bayesian statistical algorithm (Zhang et al., 2002, Nucleic Acids Res. 30:5213-21).

Exemplary traits. As discussed supra, the embodiment of the present invention illustrated in FIG. 6 provides methods for associating loci with a trait exhibited by one or more organisms in a plurality of organisms of a species (e.g., a single species). In some instances, the locus is a gene and it is associated with the trait by identifying a marker within that gene that associates with a particular phenotype exhibited by a portion of a cohort group. In some embodiments of the present invention, the trait of interest is a complex trait, such as a disease, e.g., a human disease. Exemplary diseases include without limitation allergies, asthma, and obsessive-compulsive disorders such as panic disorders, phobias, and post-traumatic stress disorders.

Exemplary diseases further include autoimmune disorders such as Addison's disease, alopecia greata, ankylosing spondylitis, antiphospholipid syndrome, Behcet's disease, chronic fatigue syndrome, Crohn's disease and ulcerative colitis, diabetes, fibromyalgia, Goodpasture syndrome, graft versus host disease, lupus, Meniere's disease, multiple sclerosis, myasthenia gravis, myositis, pemphigus vulgaris, primary biliary cirrhosis, psoriasis, rheumatic fever, sarcoidosis, scleroderma, vasculitis, vitiligo, and Wegener's granulomatosis.

Exemplary diseases further include bone diseases such as achondroplasia, bone cancer, fibrodysplasia ossificans progressiva, fibrous dysplasia, legg calve perthes disease, myeloma, osteogenesis imperfecta, osteomyelitis, osteoporosis, paget's disease, and scoliosis. Exemplary diseases include cancers such as bladder cancer, bone cancer, brain tumors, breast cancer, cervical cancer, colon cancer, gynecologic cancers, Hodgkin's disease, kidney cancer, laryngeal cancer, leukemia, liver cancer, lung cancer, lymphoma, oral cancer, ovarian cancer, pancreatic cancer, prostate cancer, skin cancer, testicular cancer, and the like.

Exemplary diseases further include genetic disorders such as achondroplasia, achromatopsia, acid maltase deficiency, adrenoleukodystrophy, Aicardi syndrome, alpha-1 antitrypsin deficiency, androgen insensitivity syndrome, Apert syndrome, dysplasia, ataxia telangiectasia, blue rubber bleb nevus syndrome, canavan disease, Cri du chat syndrome, cystic fibrosis, Dercum's disease, fanconi anemia, fibrodysplasia ossificans progressiva, fragile x syndrome, galactosemia, gaucher disease, hemochromatosis, hemophilia, Huntington's disease, Hurler syndrome, hypophosphatasia, klinefelter syndrome, Krabbes disease, Langer-Giedion syndrome, leukodystrophy, long qt syndrome, Marfan syndrome, Moebius syndrome, mucopolysaccharidosis (mps), nail patella syndrome, nephrogenic, diabetes insipidus, neurofibromatosis, Niemann-Pick disease, osteogenesis imperfecta, porphyria, Prader-Willi syndrome, progeria, proteus syndrome, retinoblastoma, Rett syndrome, rubinstein-taybi syndrome, Sanfilippo syndrome, Shwachman syndrome, sickle cell disease, Smith-Magenis syndrome, Stickler syndrome, Tay-Sachs, thrombocytopenia absent radius (tar) syndrome, Treacher collins syndrome, trisomy, tuberous sclerosis, Turner's syndrome, urea cycle disorder, Von Hippel-Lindau disease, Waardenburg syndrome, Williams syndrome, and Wilson's disease.

Exemplary diseases further include angina pectoris, dysplasia, atherosclerosis/arteriosclerosis, congenital heart disease, endocarditis, high cholesterol, hypertension, long qt syndrome, mitral valve prolapse, postural orthostatic tachycardia syndrome, and thrombosis.

Example 3

Figure 7:
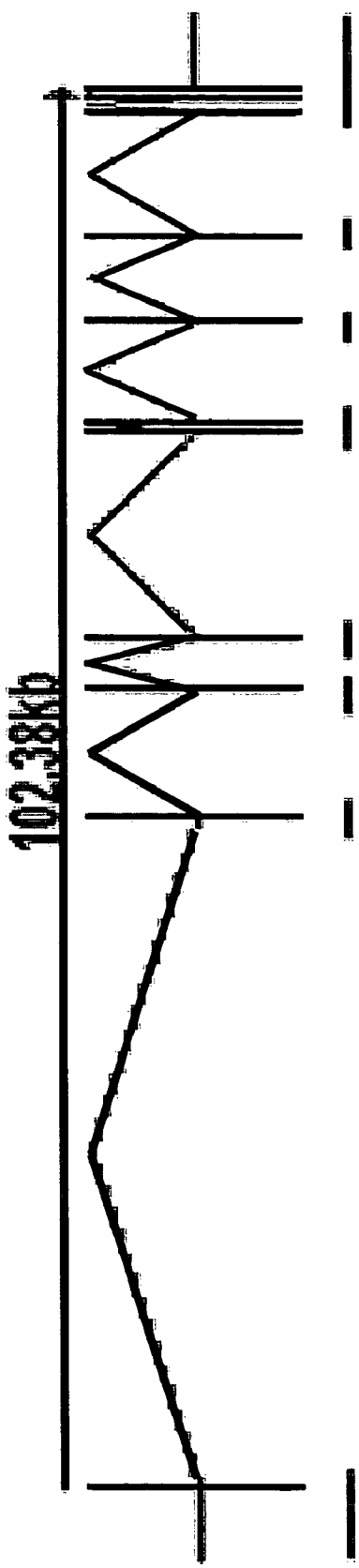
FIG. 7 illustrates the exon structure of human gene HRMT1L3. Each vertical bar represents an exon, and the short horizontal lines at the bottom indicate genomic regions covered by PCR amplification.

The methods of the present invention were tested by using the software program in the Computer Program Listing Appendix to perform SNP discovery and genotyping of the human gene HRMT1 L3 (NCBI accession number NM_019854; Strausberg et al., 2002, Proc. Natl. Acad. Sci. U.S.A. 99:16899-903) using genomic DNA samples from 32 Europeans. HRMT1L3 is a protein arginine N-methyltransferase, located on human chromosome 12, around 3.5 Mb. It has ten exons, covering a 102.38 Kb genomic region. Because most of the genomic regions covered by HRMT1L3 are intronic regions, a decision was made to only genotype its exonic and regulatory regions. A total of 48 pairs of PCR primers were designed. Together, the primers cover a total of approximately 30 Kb of genomic region as illustrated in FIG. 7.

A total of 48 PCR reactions were performed on each of the 32 European genomic DNA samples, and both strands of the resulting amplified PCR products were sequenced. In total, 48×32×2=3072 amplicons were sequenced. The length of each amplicon is about 650 bp. Therefore, about 48×32×2× 650=1996.8 Kb were sequenced. If these sequences were analyzed by a human with assistance of conventional computer software, such as Sequencher (Gene Codes Corporation, Ann Arbor, Mich.) or TraceTuner (Paracel, Pasadena, Calif.), which can analyze sequence quality, align amplicons from same genomic region and graphically display potential polymorphisms, it will still take approximately 0.5 to 1 hour for an experienced technician to examine 64 heterozygous waveforms from one primer pair, identify SNPs and collect allele information. Therefore, it will take at least 16 hours for one experienced technician to examine all these 3072 sequences, or 1996.8 Kb of sequences. Using the systems and methods of the present invention, as embodied in the computer program enclosed in the Computer Program Listing Appendix detailed in Table 1, it takes less than five minutes to completely analyze all 3072 heterozygous waveforms, or 1996.8 Kb of sequence, including quality checking, splitting heterozygous waveforms to homozygous waveforms, performing SNP discovery and collecting allele information. A total of 44 SNPs were discovered in the analyzed nucleic acid sequences.

Alternative Embodiments

The foregoing descriptions of specific embodiments of the present invention are presented for purposes of illustration and description, and are not intended to be exhaustive or to limit the invention to the precise forms disclosed. Many modifications and variations are possible in view of the above teachings. For example, reference was made to an input chromatogram 46 that includes a trace for each of the four possible bases: adenine, guanine, cytosine and thymine. However, the present invention is not limited to nucleic acid sequences having such bases. In fact, any bases, including but not limited to any purine or pyrimidine derivatives, can be used in the present invention so long as they are differentially labeled with unique fluorophores or other labeling reagents. For example, such bases include without limitation those disclosed in WO 98/16539 (Novo Nordisk A/S), WO 98/04126 (Rhone-Poulenc Rorer Pharmaceuticals Inc.), WO 98/01459 (Novo Nordisk A/S), U.S. Pat. No. 6,492,348 to Bays et al., U.S. Pat. No. 6,005,096 to Matteucci et al., Inoue et al., 1987, Jpn Kokai JP 62059293, Prober et al., 1987, Science 238:336-41, Sung, 1981, Nucl. Acids Res. 9(22):6139-51, Sung, 1982, J. Org. Chem. 47:3623-28, Draper, 1984, Nucleic Acids Res. 12(2):989-1002, Draper 1986, Anal. Biochem. 157(2):199, European Patent Application 063879, and PCT Application No. PCT/US84/00279.

REFERENCES CITED AND CONCLUSION

All references cited herein are incorporated herein by reference in their entirety and for all purposes to the same extent as if each individual publication or patent or patent application was specifically and individually indicated to be incorporated by reference in its entirety for all purposes.

The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the following claims and their equivalents.

We claim:

1. A method of processing a heterozygous input nucleic acid chromatogram from a heterozygous nucleic acid sample having a plurality of substantially simultaneous traces, each trace in said plurality of traces having a plurality of datapoints and each respective datapoint in each said plurality of datapoints representing a signal amplitude at a position in the trace corresponding to the respective datapoint, the method comprising:

identifying a first peak in a first trace in said plurality of traces that is substantially overlapping a second peak in a second trace in said plurality of traces, the substantial overlap of the first peak and the second peak thereby indicating heterozygosity in the heterozygous input nucleic acid chromatogram; and outputting said first peak to a first output homozygous representation of said heterozygous nucleic acid sample and said second peak to a second output homozygous representation of said heterozygous nucleic acid sample wherein said identifying and said outputting are executed using a suitably programmed computer.

2. The method of claim 1 wherein
said first output homozygous representation is a first homozygous sequence representation of said heterozygous input nucleic acid chromatogram; and
said second output homozygous representation is a second homozygous sequence representation of said heterozygous input nucleic acid chromatogram.

3. The method of claim 1 wherein
said first output homozygous representation is a first homozygous nucleic acid chromatogram; and
said second output homozygous representation is a second homozygous nucleic acid chromatogram.

4. The method of claim 1 wherein said identifying comprises:

(A) marking, for each respective peak of one or more peaks in said first trace, a datapoint having a maximum value in said respective peak, said one or more peaks in said first trace including said first peak;

(B) marking, for each respective peak of one or more peaks in said second trace, a datapoint having a maximum value of said respective peak, said one or more peaks in said second trace including said second peak; and (C) identifying a coordinate in said heterozygous input nucleic acid chromatogram that is within an overlap threshold number of datapoints of (i) a first datapoint having a maximal value in said first peak and (ii) a second datapoint having a maximum value in said second peak.

5. The method of claim 4 wherein said first peak is substantially overlapping said second peak when said first datapoint and said second datapoint are between two datapoints and seven datapoints apart.

6. The method of claim 4 wherein said first peak is substantially overlapping said second peak when said first datapoint and said second datapoint are less than three datapoints apart.

7. The method of claim 4 wherein, when there is more than a threshold number of peaks in said heterozygous input nucleic acid chromatogram in a predetermined region about said coordinate, said first peak and said second peak are each written to both said first output homozygous representation and said second output homozygous representation.

8. The method of claim 7 wherein said threshold number of peaks is between two peaks and five peaks.

9. The method of claim 7 wherein said predetermined region is between 2 datapoints and 20 datapoints about said coordinate.

10. The method of claim 4 wherein, when a ratio between said first datapoint of said first peak and said second datapoint of said second peak is greater than a threshold ratio value, said first peak and said second peak are each written to said first output homozygous representation and said second output homozygous representation.

11. The method of claim 10 wherein said threshold ratio value is at least 0.20.

12. The method of claim 10 wherein said threshold ratio value is at least 0.40.

13. The method of claim 4 wherein, when a ratio between said first datapoint of said first peak and said second datapoint of said second peak is less than a threshold ratio value, said first peak and said second peak are each written to said first output homozygous representation and said second output homozygous representation.

14. The method of claim 4, the method further comprising:
    determining an average peak background value for said heterozygous input nucleic acid chromatogram, and
    writing said first peak and said second peak to said first output homozygous representation and said second output homozygous representation when either said first datapoint of said first peak or said second datapoint of said second peak is less than said average peak background value.

15. The method of claim 14 wherein the average peak background value is calculated by:
    (i) comparing (a) a datapoint in a test trace in said plurality of traces that has a maximal value of a peak in said test trace to (b) the corresponding datapoint that has a maximal value in a corresponding region of another trace in said plurality of traces;
    (ii) repeating the comparison of said datapoint in said test trace to the corresponding datapoint that has a maximal value in a corresponding region of another trace in said plurality of traces until each trace in said plurality of traces has been compared in said comparing (i), wherein when said datapoint in said test trace has a value that is larger than the value held by the corresponding datapoint of each other trace in said plurality of traces, the value of said datapoint is added to a counter;
    (iii) repeating the comparing (i) and the repeating (ii) using a different datapoint that has a maximal value of a different peak in said test trace until all or a portion of the peaks in said test trace have been compared by said comparing (i);
    (iv) repeating said comparing (i), said repeating (ii), and said repeating (iii) using a different test trace in said plurality of traces until each trace in said plurality of traces has been considered as a test trace in said comparing (i); and
    (v) averaging said counter by a number of peaks added to said counter thereby obtaining said average peak background value.

16. The method of claim 4, wherein said heterozygous input nucleic acid chromatogram represents a nucleic acid sequence from a heterozygous nucleic acid sample, the method further comprising:
    scanning said heterozygous input nucleic chromatogram for a point of insertion or deletion in said heterozygous nucleic acid sample; wherein
    when said a point of insertion or deletion is found and said coordinate is after said point, said first peak and said second peak are each written to said first output homozygous representation and said second output homozygous representation.

17. The method of claim 16 wherein said scanning comprises counting a number of peaks that occur in said plurality of traces after said coordinate, wherein when said number of peaks exceeds an insertion/deletion threshold number, said coordinate is determined to be said point of insertion or deletion in said heterozygous nucleic acid sample.

18. The method of claim 17 wherein said insertion/deletion threshold number is between 25 and 75.

19. The method of claim 17 wherein said insertion/deletion threshold number is between 75 and 200.

20. The method of claim 19 wherein said scanning comprises determining the percentage of peaks that overlap in said plurality of traces after said coordinate, wherein, when said percentage of peaks that overlap exceeds an insertion/deletion threshold percentage, said coordinate is determined to be said point of insertion or deletion in said heterozygous nucleic acid sample.

21. The method of claim 20 wherein said insertion/deletion threshold percentage is between two percent and ninety percent.

22. The method of claim 20 wherein said insertion/deletion threshold percentage is between ten percent and fifty percent.

23. The method of claim 1 wherein said first peak and said second peak each independently consist of between five datapoints and forty datapoints.

24. The method of claim 1 wherein said heterozygous input nucleic acid chromatogram is in an ABI trace file format, a SCF file format, a ZTR file format, or an ALF file format.

25. The method of claim 1 wherein said first output homozygous representation and said second output homozygous representation are each written in an ABI trace file format, a SCF file format, a ZTR file format, or an ALF file format.

26. The method of claim 1 wherein said heterozygous input nucleic acid chromatogram represents a nucleic acid sequence from a heterozygous nucleic acid sample and wherein, prior to said outputting, said method comprises multiplying said first peak and said second peak by a scaling constant.

27. The method of claim 26 wherein said scaling constant is between 1.1 and 3.2.

28. The method of claim 26 wherein said scaling constant is 2.0.

29. The method of claim 1, the method further comprising:
    generating a common peak profile for a plurality of peaks in said heterozygous input nucleic acid chromatogram; and
    checking, prior to said outputting, said first peak or said second peak against said common peak profile.

30. The method of claim 29 wherein said generating comprises:
    determining the average number of datapoints in the peaks in said heterozygous input nucleic acid chromatogram; and
    averaging a profile of all or a portion of the peaks in said heterozygous input nucleic acid chromatogram that have said average number of datapoints, thereby forming said common peak profile.

31. The method of claim 29 wherein said checking comprises determining whether a value of a test datapoint in said first peak or said second peak exceeds, by an error percentage, a value of the datapoint in said common peak profile that corresponds to said test datapoint.

32. The method of claim 31 wherein said error percentage is between 0.01 and 0.4.

33. The method of claim 31 wherein said error percentage is 0.1.

34. The method of claim 1 wherein said plurality of traces in said heterozygous input nucleic acid chromatogram nucleic acid consists of a first trace for guanine, a second trace for cytosine, a third trace for adenosine and a fourth trace for thymine.

35. A tangible computer readable medium having computer-executable instructions for performing the steps of the method of claim 1.

36. A computer program product for use in conjunction with a computer system, the computer program product comprising a computer readable storage medium and a computer program mechanism embedded therein, the computer program mechanism for processing a heterozygous input nucleic acid chromatogram from a heterozygous nucleic acid sample having a plurality of substantially simultaneous traces, the computer program mechanism comprising executable instructions for:
   identifying a first peak in a first trace in said plurality of traces that is substantially overlapping a second peak in a second trace in said plurality of traces, the substantial overlap of the first peak and the second peak thereby indicating heterozygosity in the heterozygous input nucleic acid chromatogram; and
   outputting said first peak to a first output homozygous representation of said heterozygous nucleic acid sample and said second peak to a second output homozygous representation of said heterozygous nucleic acid sample wherein said first output homozygous representation and said second output homozygous representation are outputted or are displayed.

37. The computer program product of claim 36 wherein said first output homozygous representation is a first homozygous sequence representation of said heterozygous input nucleic acid chromatogram; and
   said second output homozygous representation is a second homozygous sequence representation of said heterozygous input nucleic acid chromatogram.

38. The computer program product of claim 36 wherein said first output homozygous representation is a first homozygous nucleic acid chromatogram; and
   said second output homozygous representation is a second homozygous nucleic acid chromatogram.

39. The computer program product of claim 36 wherein said instructions for identifying comprise:
   (A) instructions for marking, for each respective peak of one or more peaks in said first trace, a datapoint having a maximum value in said respective peak, said one or more peaks in said first trace including said first peak;
   (B) instructions for marking, for each respective peak of one or more peaks in said second trace, a datapoint having a maximum value of said respective peak, said one or more peaks in said second trace including said second peak; and
   (C) instructions for identifying a coordinate in said heterozygous input nucleic acid chromatogram that is within an overlap threshold number of datapoints of (i) a first datapoint having a maximal value in said first peak and (ii) a second datapoint having a maximum value in said second peak.

40. A computer system for processing a heterozygous input nucleic acid chromatogram from a heterozygous nucleic acid sample having a plurality of substantially simultaneous traces, the computer system comprising:
   a central processing unit;
   a memory, coupled to the central processing unit, the memory storing:
   said heterozygous input nucleic acid chromatogram; and
   a program module, said program module comprising executable instructions for:
      identifying a first peak in a first trace in said plurality of traces that is substantially overlapping a second peak in a second trace in said plurality of traces, the substantial overlap of the first peak and the second peak thereby indicating heterozygosity in the heterozygous input nucleic acid chromatogram; and
      outputting said first peak to a first output homozygous representation of said heterozygous nucleic acid sample and said second peak to a second output homozygous representation of said heterozygous nucleic acid sample wherein said first output homozygous representation and said second output homozygous representation are outputted, or are displayed.

41. The computer system of claim 40 wherein
   said first output homozygous representation is a first homozygous sequence representation of said heterozygous input nucleic acid chromatogram; and
   said second output homozygous representation is a second homozygous sequence representation of said heterozygous input nucleic acid chromatogram.

42. The computer system of claim 40 wherein
   said first output homozygous representation is a first homozygous nucleic acid chromatogram; and
   said second output homozygous representation is a second homozygous nucleic acid chromatogram.

43. The computer system of claim 40 wherein said identifying comprises:
   (A) instructions for marking, for each respective peak of one or more peaks in said first trace, a datapoint having a maximum value in said respective peak, said one or more peaks in said first trace including said first peak;
   (B) instructions for marking, for each respective peak of one or more peaks in said second trace, a datapoint having a maximum value of said respective peak, said one or more peaks in said second trace including said second peak; and
   (C) instructions for identifying a coordinate in said heterozygous input nucleic acid chromatogram that is within an overlap threshold number of datapoints of (i) a first datapoint having a maximal value in said first peak and (ii) a second datapoint having a maximum value in said second peak.

* * * * *

SEQUENCE LISTING

```
<160> NUMBER OF SEQ ID NOS: 3

<210> SEQ ID NO 1
<211> LENGTH: 30
<212> TYPE: DNA
<213> ORGANISM: Unknown
<220> FEATURE:
<223> OTHER INFORMATION: sample sequence illustrates an
      input chromatogram
```

-continued

```
<400> SEQUENCE: 1
tcagacacac cagccctggc agcggctggg                                          30

<210> SEQ ID NO 2
<211> LENGTH: 30
<212> TYPE: DNA
<213> ORGANISM: Unknown
<220> FEATURE:
<223> OTHER INFORMATION: sample sequence illustrates an
      input chromatogram

<400> SEQUENCE: 2
tcagacacac cagccgtggc agcggctggg                                          30

<210> SEQ ID NO 3
<211> LENGTH: 108
<212> TYPE: DNA
<213> ORGANISM: Unknown
<220> FEATURE:
<223> OTHER INFORMATION: sample sequence illustrates an
      input chromatogram
<220> FEATURE:
<221> NAME/KEY: misc_feature
<222> LOCATION: 16, 20, 32, 33, 52, 56, 68, 69, 88, 92, 104, 105
<223> OTHER INFORMATION: n = A,T,C or G

<400> SEQUENCE: 3
tgccgatact cccaanccgn ttctttccaa annaagtgcc gatactccca anccgnttct          60
ttccaaanna agtgccgata ctcccaancc gnttctttcc aaannaag                     108
```